United States Patent
Cabantous et al.

(10) Patent No.: US 10,782,304 B2
(45) Date of Patent: Sep. 22, 2020

(54) METHODS FOR DETECTING PROTEIN-PROTEIN INTERACTIONS

(71) Applicants: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR)

(72) Inventors: Stéphanie Cabantous, Toulouse (FR); Faten Koraïchi, Toulouse (FR); Gilles Favre, Toulouse (FR)

(73) Assignees: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR)

( * ) Notice: Subject to any disclaimer, the term of this patent is extended or adjusted under 35 U.S.C. 154(b) by 220 days.

(21) Appl. No.: 15/736,200

(22) PCT Filed: Jun. 23, 2016

(86) PCT No.: PCT/EP2016/064612
§ 371 (c)(1),
(2) Date: Dec. 13, 2017

(87) PCT Pub. No.: WO2016/207313
PCT Pub. Date: Dec. 29, 2016

(65) Prior Publication Data
US 2018/0164324 A1 Jun. 14, 2018

(30) Foreign Application Priority Data

Jun. 24, 2015 (EP) .................................... 15305971
Sep. 30, 2015 (EP) .................................... 15306542

(51) Int. Cl.
| | |
|---|---|
| *G01N 33/68* | (2006.01) |
| *G01N 33/542* | (2006.01) |
| *C07K 16/18* | (2006.01) |
| *C40B 30/04* | (2006.01) |
| *G01N 33/50* | (2006.01) |
| *G01N 33/533* | (2006.01) |

(52) U.S. Cl.
CPC ......... *G01N 33/6845* (2013.01); *C07K 16/18* (2013.01); *C40B 30/04* (2013.01); *G01N 33/5008* (2013.01); *G01N 33/533* (2013.01); *G01N 33/542* (2013.01); *C07K 2319/70* (2013.01)

(58) Field of Classification Search
CPC combination set(s) only.
See application file for complete search history.

(56) References Cited

U.S. PATENT DOCUMENTS

| | | | |
|---|---|---|---|
| 7,666,606 B2 * | 2/2010 | Waldo ..................... | C40B 30/04 435/455 |
| 7,763,418 B2 | 7/2010 | Cheng et al. | |
| 2015/0099271 A1 | 4/2015 | Waldo et al. | |

FOREIGN PATENT DOCUMENTS

EP    1 785 434 B2    5/2007

OTHER PUBLICATIONS

Ferrara et al., Flourscent Labeling of Antibody Fragments Using Split GFP, PLoS One, 2011, 6(10), 1-9. (Year: 2011).*
Giusti et al.—Somatic diversification of S107 from an antiphosphocholine to an anti-DNA autoantibody is due to a single base change in its heavy chain variable region. Proc. Natl. Acad. Sci. USA, 84, 2926-2930, 1987. (Year: 1987).*
Kirchhofer et al, "Modulation of protein properties in living cells using nanobodies", Nature Structural & Molecular Biology, Dec. 13, 2009, pp. 133-138, vol. 17, No. 1.
Kaiser et al, "Recent progress in generating intracellular functional antibody fragments to target and trace cellular components in living cells", Biochimica Et Biophysica Acta (BBA)—Proteins & Proteomics, May 2, 2014, pp. 1933-1942, vol. 1844, No. 11.

* cited by examiner

*Primary Examiner* — Elly-Gerald Stoica
(74) *Attorney, Agent, or Firm* — W&C IP

(57) ABSTRACT

The present invention relates to methods and kits for detection protein-protein interactions. In particular, the present invention relates to a method for detecting the binding between a first polypeptide (A) and a second polypeptide (B) in a cell comprising i) providing a cell that expresses (a) a polypeptide (GFP1-9) comprising an amino acid sequence having at least 90% of identity with the amino acid sequence selected from the group consisting of SEQ ID NO: 1-4 (b) a first fusion protein wherein the polypeptide (A) is fused to a polypeptide (GFP10) having an amino an amino acid sequence having at least 90% of identity with the amino acid sequence selected from the group consisting of SEQ ID NO:5-7 (c) a second fusion protein wherein the polypeptide (B) is fused to a polypeptide (GFP11) having an amino an amino acid sequence having at least 90% of identity with the amino acid sequence selected from the group consisting of SEQ ID NO: 8-9 and (d) an intrabody specific for the complex formed by the self-assembly of the first, second and third polypeptides (a), (b) and (c) ii) detecting the fluorescence wherein when the fluorescence is detected it is concluded that the polypeptide (A) binds to polypeptide (B) and wherein the fluorescence is not detected it is concluded that the polypeptides (A) does not bind to polypeptide (B).

Figure 1A:
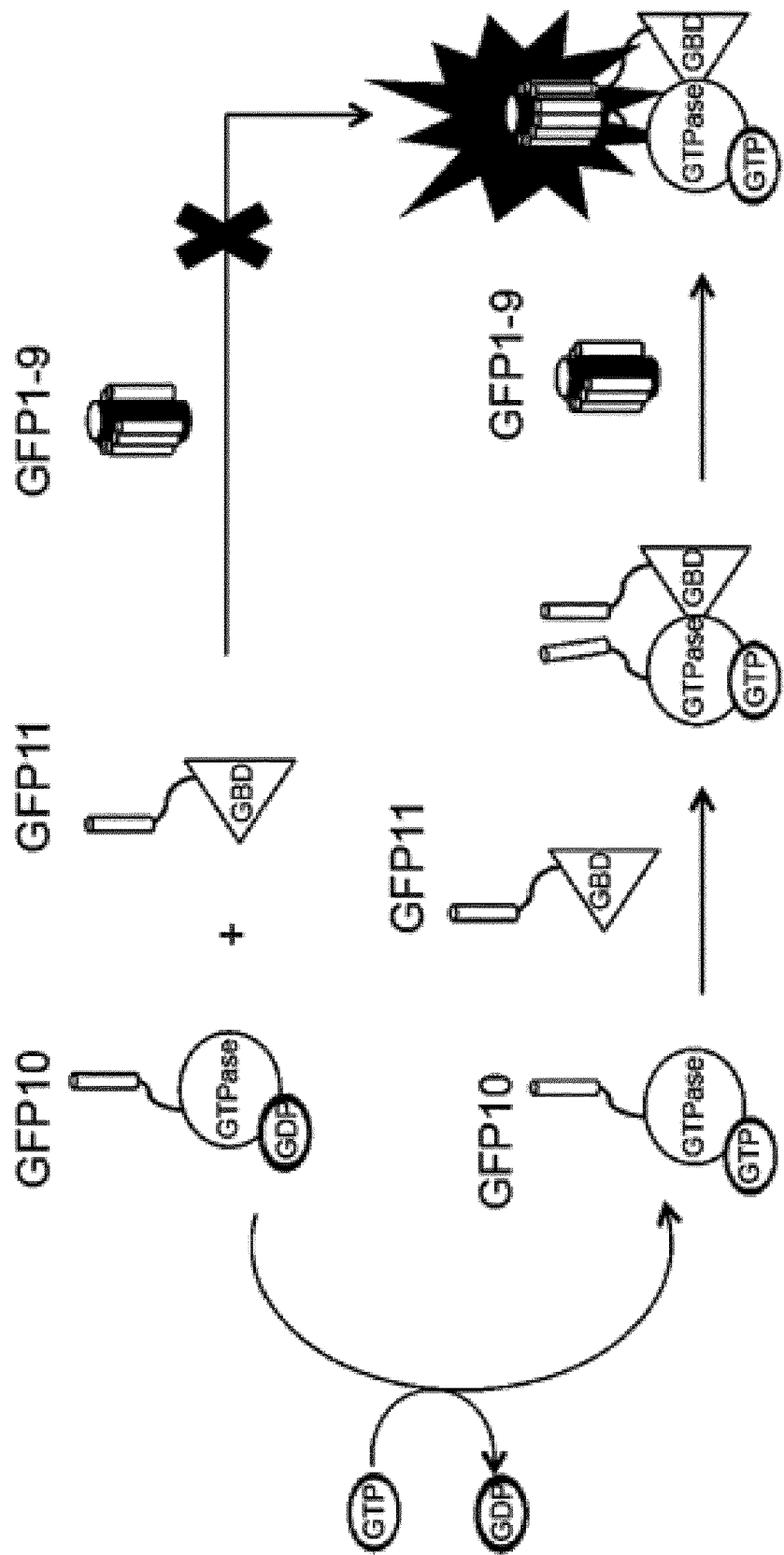

16 Claims, 10 Drawing Sheets
Specification includes a Sequence Listing.

SEQUENCE LISTING

<160> NUMBER OF SEQ ID NOS: 19

<210> SEQ ID NO 1
<211> LENGTH: 196
<212> TYPE: PRT
<213> ORGANISM: Artificial Sequence
<220> FEATURE:
<223> OTHER INFORMATION: GFP1-9 OPT WT

<400> SEQUENCE: 1

Met Arg Lys Gly Glu Glu Leu Phe Thr Gly Val Val Pro Ile Leu Ile
1               5                   10                  15

Glu Leu Asp Gly Asp Val Asn Gly His Lys Phe Phe Val Arg Gly Glu
            20                  25                  30

Gly Glu Gly Asp Ala Thr Asn Gly Lys Leu Ser Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro
        195

<210> SEQ ID NO 2
<211> LENGTH: 196
<212> TYPE: PRT
<213> ORGANISM: Artificial Sequence
<220> FEATURE:
<223> OTHER INFORMATION: GFP1-9 OPT1

<400> SEQUENCE: 2

Met Arg Lys Gly Glu Glu Leu Phe Thr Gly Val Val Pro Ile Leu Ile
1               5                   10                  15

Glu Leu Asp Gly Asp Val Asn Gly His Lys Phe Phe Val Arg Gly Glu
            20                  25                  30

Gly Glu Gly Asp Ala Thr Ile Gly Lys Leu Ser Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

```
Thr Ile Tyr Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Lys Val Tyr Ile Thr Ala Asp Lys Gln Asn Asn Gly
145                 150                 155                 160

Ile Lys Ala Asn Phe Thr Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro
        195

<210> SEQ ID NO 3
<211> LENGTH: 196
<212> TYPE: PRT
<213> ORGANISM: Artificial Sequence
<220> FEATURE:
<223> OTHER INFORMATION: GFP1-9 OPT2

<400> SEQUENCE: 3

Met Arg Lys Gly Glu Glu Leu Phe Thr Gly Val Val Pro Ile Leu Ile
1               5                   10                  15

Glu Leu Asp Gly Asp Val Asn Gly His Lys Phe Phe Val Arg Gly Glu
            20                  25                  30

Gly Glu Gly Asp Ala Thr Ile Gly Lys Leu Ser Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Tyr Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Pro His Asn Val Tyr Ile Thr Ala Asp Lys Gln Lys Asn Gly
145                 150                 155                 160

Ile Lys Ala Asn Phe Thr Ile Arg His Asn Val Glu Asp Gly Ser Val
                165                 170                 175

Gln Leu Ala Glu His Tyr Gln Gln Asn Thr Pro Ile Gly Asp Gly Pro
            180                 185                 190

Val Leu Leu Pro
        195

<210> SEQ ID NO 4
<211> LENGTH: 195
<212> TYPE: PRT
<213> ORGANISM: Artificial Sequence
<220> FEATURE:
<223> OTHER INFORMATION: GFP1-9 OPT3
```

-continued

```
<400> SEQUENCE: 4

Met Val Arg Lys Gly Glu Glu Leu Phe Thr Gly Val Val Pro Ile Leu
1               5                   10                  15

Ile Glu Leu Asp Gly Asp Val Asn Gly His Lys Phe Val Arg Gly
            20                  25                  30

Glu Gly Glu Gly Asp Ala Thr Ile Gly Lys Leu Ser Leu Lys Phe Ile
        35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65              70                  75                  80

Arg His Asp Phe Phe Lys Ser Ala Met Pro Glu Gly Tyr Val Gln Glu
                85                  90                  95

Arg Thr Ile Tyr Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Lys Val Tyr Ile Thr Ala Asp Lys Gln Asn Asn
145                 150                 155                 160

Gly Ile Lys Ala Asn Phe Thr Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Asp
    195

<210> SEQ ID NO 5
<211> LENGTH: 20
<212> TYPE: PRT
<213> ORGANISM: Artificial Sequence
<220> FEATURE:
<223> OTHER INFORMATION: GFP10

<400> SEQUENCE: 5

Met Gly Leu Pro Asp Asn His Tyr Leu Ser Thr Gln Ser Val Leu Ser
1               5                   10                  15

Lys Asp Pro Asn
            20

<210> SEQ ID NO 6
<211> LENGTH: 20
<212> TYPE: PRT
<213> ORGANISM: Artificial Sequence
<220> FEATURE:
<223> OTHER INFORMATION: GFP10

<400> SEQUENCE: 6

Met Asp Leu Pro Asp Asn His Tyr Leu Ser Thr Gln Thr Ile Leu Leu
1               5                   10                  15

Lys Asp Leu Asn
            20

<210> SEQ ID NO 7
<211> LENGTH: 20
<212> TYPE: PRT
<213> ORGANISM: Artificial Sequence
```

-continued

```
<220> FEATURE:
<223> OTHER INFORMATION: GFP10

<400> SEQUENCE: 7

Met Asp Leu Pro Asp His Tyr Leu Ser Thr Gln Thr Ile Leu Ser
1               5                   10                  15

Lys Asp Leu Asn
            20

<210> SEQ ID NO 8
<211> LENGTH: 21
<212> TYPE: PRT
<213> ORGANISM: Artificial Sequence
<220> FEATURE:
<223> OTHER INFORMATION: GFP11

<400> SEQUENCE: 8

Glu Lys Arg Asp His Met Val Leu Leu Glu Phe Val Thr Ala Ala Gly
1               5                   10                  15

Ile Thr Gly Ala Ser
            20

<210> SEQ ID NO 9
<211> LENGTH: 21
<212> TYPE: PRT
<213> ORGANISM: Artificial Sequence
<220> FEATURE:
<223> OTHER INFORMATION: GFP11

<400> SEQUENCE: 9

Glu Lys Arg Asp His Met Val Leu Leu Glu Tyr Val Thr Ala Ala Gly
1               5                   10                  15

Ile Thr Asp Ala Ser
            20

<210> SEQ ID NO 10
<211> LENGTH: 227
<212> TYPE: PRT
<213> ORGANISM: Artificial Sequence
<220> FEATURE:
<223> OTHER INFORMATION: GFP10-RhoA
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid

<400> SEQUENCE: 10

Met Gly Asp Leu Pro Asp His Tyr Leu Ser Thr Gln Thr Ile Leu
1               5                   10                  15

Ser Lys Asp Leu Asn Ile Asp Gly Gly Gly Ser Gly Gly Gly Gly
                20                  25                  30

Ser Ser Gly Ala Ala Ile Arg Lys Lys Leu Val Ile Val Gly Asp Gly
            35                  40                  45

Ala Cys Gly Lys Thr Cys Leu Leu Ile Val Phe Ser Lys Asp Gln Phe
50                  55                  60

Pro Glu Val Tyr Val Pro Thr Val Phe Glu Asn Tyr Val Ala Asp Ile
65                  70                  75                  80

Glu Val Asp Gly Lys Gln Val Glu Leu Ala Leu Trp Asp Thr Ala Gly
                85                  90                  95
```

```
Gln Glu Asp Tyr Asp Arg Leu Arg Pro Leu Ser Tyr Pro Asp Thr Asp
            100                 105                 110

Val Ile Leu Met Cys Phe Ser Ile Asp Ser Pro Asp Ser Leu Xaa Asn
            115                 120                 125

Ile Pro Xaa Lys Trp Thr Pro Glu Val Lys His Phe Cys Pro Asn Val
            130                 135                 140

Pro Ile Ile Leu Val Gly Asn Lys Lys Asp Leu Arg Asn Asp Glu His
145                 150                 155                 160

Thr Arg Arg Glu Leu Ala Lys Met Lys Gln Glu Pro Val Lys Pro Glu
            165                 170                 175

Glu Gly Arg Asp Met Ala Asn Arg Ile Gly Ala Phe Gly Tyr Met Glu
            180                 185                 190

Cys Ser Ala Lys Thr Lys Asp Gly Val Arg Glu Val Phe Glu Met Ala
            195                 200                 205

Thr Arg Ala Ala Leu Gln Ala Arg Arg Gly Lys Lys Lys Ser Gly Cys
            210                 215                 220

Leu Val Leu
225

<210> SEQ ID NO 11
<211> LENGTH: 230
<212> TYPE: PRT
<213> ORGANISM: Artificial Sequence
<220> FEATURE:
<223> OTHER INFORMATION: GFP10-RhoB

<400> SEQUENCE: 11

Met Gly Asp Leu Pro Asp Asp His Tyr Leu Ser Thr Gln Thr Ile Leu
1               5                   10                  15

Ser Lys Asp Leu Asn Ile Asp Gly Gly Gly Ser Gly Gly Gly Gly
            20                  25                  30

Ser Ser Gly Ala Ala Ile Arg Lys Lys Leu Val Val Val Gly Asp Gly
            35                  40                  45

Ala Cys Gly Lys Thr Cys Leu Leu Ile Val Phe Ser Lys Asp Glu Phe
50                  55                  60

Pro Glu Val Tyr Val Pro Thr Val Phe Glu Asn Tyr Val Ala Asp Ile
65                  70                  75                  80

Glu Val Asp Gly Lys Gln Val Glu Leu Ala Leu Trp Asp Thr Ala Gly
            85                  90                  95

Gln Glu Asp Tyr Asp Arg Leu Arg Pro Leu Ser Tyr Pro Asp Thr Asp
            100                 105                 110

Val Ile Leu Met Cys Phe Ser Val Asp Ser Pro Asp Ser Leu Glu Asn
            115                 120                 125

Ile Pro Glu Lys Trp Val Pro Glu Val Lys His Phe Cys Pro Asn Val
            130                 135                 140

Pro Ile Ile Leu Val Ala Asn Lys Lys Asp Leu Arg Ser Asp Glu His
145                 150                 155                 160

Val Arg Thr Glu Leu Ala Arg Met Lys Gln Glu Pro Val Arg Thr Asp
            165                 170                 175

Asp Gly Arg Ala Met Ala Val Arg Ile Gln Ala Tyr Asp Tyr Leu Glu
            180                 185                 190

Cys Ser Ala Lys Thr Lys Glu Gly Val Arg Glu Val Phe Glu Thr Ala
            195                 200                 205
```

```
Thr Arg Ala Ala Leu Gln Lys Arg Tyr Gly Ser Gln Asn Gly Cys Ile
    210                 215                 220

Asn Cys Cys Lys Val Leu
225                 230
```

<210> SEQ ID NO 12
<211> LENGTH: 223
<212> TYPE: PRT
<213> ORGANISM: Artificial Sequence
<220> FEATURE:
<223> OTHER INFORMATION: GFP10-HRas

<400> SEQUENCE: 12

```
Met Gly Asp Leu Pro Asp Asp His Tyr Leu Ser Thr Gln Thr Ile Leu
1               5                   10                  15

Ser Lys Asp Leu Asn Ile Asp Gly Gly Gly Ser Gly Gly Gly Gly Gly
                20                  25                  30

Ser Ser Gly Thr Glu Tyr Lys Leu Val Val Gly Ala Gly Gly Val
            35                  40                  45

Gly Lys Asn Ala Leu Thr Ile Gln Leu Ile Gln Asn His Phe Val Asp
    50                  55                  60

Glu Tyr Asp Pro Thr Ile Glu Asp Ser Tyr Arg Lys Gln Val Val Ile
65                  70                  75                  80

Asp Gly Glu Thr Cys Leu Leu Asp Ile Leu Asp Thr Ala Gly Gln Glu
                85                  90                  95

Glu Tyr Ser Ala Met Arg Asp Gln Tyr Met Arg Thr Gly Glu Gly Phe
            100                 105                 110

Leu Cys Val Phe Ala Ile Asn Asn Thr Lys Ser Phe Glu Asp Ile His
        115                 120                 125

Gln Tyr Arg Glu Gln Ile Lys Arg Val Lys Asp Ser Asp Val Pro
    130                 135                 140

Met Val Leu Val Gly Asn Lys Cys Asp Leu Ala Ala Arg Thr Val Glu
145                 150                 155                 160

Ser Arg Gln Ala Gln Asp Leu Ala Arg Ser Tyr Gly Ile Pro Tyr Ile
                165                 170                 175

Glu Thr Ser Ala Lys Thr Arg Gln Gly Val Glu Asp Ala Phe Tyr Thr
            180                 185                 190

Leu Val Arg Glu Ile Arg Gln His Lys Leu Arg Lys Leu Asn Pro Pro
        195                 200                 205

Asp Glu Ser Gly Pro Gly Cys Met Ser Cys Lys Cys Val Leu Ser
    210                 215                 220
```

<210> SEQ ID NO 13
<211> LENGTH: 232
<212> TYPE: PRT
<213> ORGANISM: Artificial Sequence
<220> FEATURE:
<223> OTHER INFORMATION: GFP10-NRas

<400> SEQUENCE: 13

```
Met Gly Asp Leu Pro Asp Asp His Tyr Leu Ser Thr Gln Thr Ile Leu
1               5                   10                  15

Ser Lys Asp Leu Asn Ile Asp Gly Ala Gly Gly Ser Pro Gly Gly Gly
                20                  25                  30

Ser Gly Gly Ser Gly Ser Gly Gly Gly Gly Ser Gly Thr Glu Tyr Lys
            35                  40                  45
```

Leu Val Val Gly Ala Gly Val Gly Lys Ser Ala Leu Thr Ile
 50                  55                  60

Gln Leu Ile Gln Asn His Phe Val Asp Glu Tyr Asp Pro Thr Ile Glu
 65                  70                  75                  80

Asp Ser Tyr Arg Lys Gln Val Val Ile Asp Gly Glu Thr Cys Leu Leu
                 85                  90                  95

Asp Ile Leu Asp Thr Ala Gly Gln Glu Glu Tyr Ser Ala Met Arg Asp
            100                 105                 110

Gln Tyr Met Arg Thr Gly Glu Gly Phe Leu Cys Val Phe Ala Ile Asn
        115                 120                 125

Asn Ser Lys Ser Phe Ala Asp Ile Asn Leu Tyr Arg Glu Gln Ile Lys
130                 135                 140

Arg Val Lys Asp Ser Asp Val Pro Met Val Leu Val Gly Asn Lys
145                 150                 155                 160

Cys Asp Leu Pro Thr Arg Thr Val Asp Thr Lys Gln Ala His Glu Leu
                165                 170                 175

Ala Lys Ser Tyr Gly Ile Pro Phe Ile Glu Thr Ser Ala Lys Thr Arg
            180                 185                 190

Gln Gly Val Glu Asp Ala Phe Tyr Thr Leu Val Arg Glu Ile Arg Gln
        195                 200                 205

Tyr Arg Met Lys Lys Leu Asn Ser Ser Asp Asp Gly Thr Gln Gly Cys
210                 215                 220

Met Gly Leu Pro Cys Val Val Met
225                 230

<210> SEQ ID NO 14
<211> LENGTH: 119
<212> TYPE: PRT
<213> ORGANISM: Artificial Sequence
<220> FEATURE:
<223> OTHER INFORMATION: Rho-binding domain of Rhotekin (RBD)-GFP11

<400> SEQUENCE: 14

Met Ile Leu Glu Asp Leu Asn Met Leu Tyr Ile Arg Gln Met Ala Leu
 1               5                  10                  15

Ser Leu Glu Asp Thr Glu Leu Gln Arg Lys Leu Asp His Glu Ile Arg
                20                  25                  30

Met Arg Asp Gly Ala Cys Lys Leu Leu Ala Ala Cys Ser Gln Arg Glu
            35                  40                  45

Gln Ala Leu Glu Ala Thr Lys Ser Leu Leu Val Cys Asn Ser Arg Ile
        50                  55                  60

Leu Ser Tyr Met Gly Glu Leu Gln Arg Arg Lys Glu Ala Gln Val Leu
 65                  70                  75                  80

Glu Lys Thr Gly Ile Asp Gly Gly Gly Ser Gly Gly Gly Ser
                85                  90                  95

Ser Gly Glu Lys Arg Asp His Met Val Leu Leu Glu Tyr Val Thr Ala
                100                 105                 110

Ala Gly Ile Thr Asp Ala Ser
        115

<210> SEQ ID NO 15
<211> LENGTH: 189
<212> TYPE: PRT
<213> ORGANISM: Artificial Sequence
<220> FEATURE:
<223> OTHER INFORMATION: Ras binding domain of c-Raf (RsBD)-GFP11

<400> SEQUENCE: 15

```
Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Ala Ser Asp Gly Lys Leu
        35                  40                  45

Thr Asp Pro Ser Lys Thr Ser Asn Thr Ile Arg Val Phe Leu Pro Asn
    50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
    130                 135                 140

Thr Phe Leu Lys Leu Gly Ile His Arg Asp Ile Asp Gly Gly Gly Gly
145                 150                 155                 160

Ser Gly Gly Gly Ser Ser Gly Glu Lys Arg Asp His Met Val Leu
                165                 170                 175

Leu Glu Tyr Val Thr Ala Ala Gly Ile Thr Asp Ala Ser
            180                 185
```

<210> SEQ ID NO 16
<211> LENGTH: 145
<212> TYPE: PRT
<213> ORGANISM: Artificial Sequence
<220> FEATURE:
<223> OTHER INFORMATION: VHH

<400> SEQUENCE: 16

```
Met Asp Gln Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Arg Trp Tyr Arg Gln Ala Pro Gly Lys Glu Arg Glu
        35                  40                  45

Trp Val Ala Gly Met Ser Ser Ala Gly Asp Arg Ser Ser Tyr Glu Asp
    50                  55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
                85                  90                  95

Tyr Cys Asn Val Asn Val Gly Phe Glu Tyr Trp Gly Gln Gly Thr Gln
            100                 105                 110

Val Thr Val Ser Ser Ala Ala Ala His His His His His Gly Ala
        115                 120                 125

Ala Glu Gln Lys Leu Ile Ser Glu Glu Asp Leu Asn Gly Gly Ser Pro
    130                 135                 140

Gly
145
```

-continued

```
<210> SEQ ID NO 17
<211> LENGTH: 225
<212> TYPE: PRT
<213> ORGANISM: Artificial Sequence
<220> FEATURE:
<223> OTHER INFORMATION: GFP10-Rac1

<400> SEQUENCE: 17

Met Gly Asp Leu Pro Asp Asp His Tyr Leu Ser Thr Gln Thr Ile Leu
1               5                   10                  15

Ser Lys Asp Leu Asn Ile Asp Gly Gly Gly Ser Gly Gly Gly Gly
            20                  25                  30

Ser Ser Gly Ala Ile Lys Cys Val Val Gly Asp Gly Ala Val Gly
        35                  40                  45

Lys Thr Cys Leu Leu Ile Ser Tyr Thr Thr Asn Ala Phe Pro Gly Glu
50                  55                  60

Tyr Ile Pro Thr Val Phe Asp Asn Tyr Ser Ala Asn Val Met Val Asp
65                  70                  75                  80

Gly Lys Pro Val Asn Leu Gly Leu Trp Asp Thr Ala Gly Gln Glu Asp
                85                  90                  95

Tyr Asp Arg Leu Arg Pro Leu Ser Tyr Pro Gln Thr Asp Val Phe Leu
            100                 105                 110

Ile Cys Phe Ser Leu Val Ser Pro Ala Ser Phe Glu Asn Val Arg Ala
        115                 120                 125

Lys Trp Tyr Pro Glu Val Arg His His Cys Pro Asn Thr Pro Ile Ile
130                 135                 140

Leu Val Gly Thr Lys Leu Asp Leu Arg Asp Asp Lys Asp Thr Ile Glu
145                 150                 155                 160

Lys Leu Lys Glu Lys Lys Leu Thr Pro Ile Thr Tyr Pro Gln Gly Leu
                165                 170                 175

Ala Met Ala Lys Glu Ile Gly Ala Val Lys Tyr Leu Glu Cys Ser Ala
            180                 185                 190

Leu Thr Gln Arg Gly Leu Lys Thr Val Phe Asp Glu Ala Ile Arg Ala
        195                 200                 205

Val Leu Cys Pro Pro Pro Val Lys Lys Arg Lys Arg Lys Cys Leu Leu
210                 215                 220

Leu
225

<210> SEQ ID NO 18
<211> LENGTH: 225
<212> TYPE: PRT
<213> ORGANISM: Artificial Sequence
<220> FEATURE:
<223> OTHER INFORMATION: GFP10-Cdc42

<400> SEQUENCE: 18

Met Gly Asp Leu Pro Asp Asp His Tyr Leu Ser Thr Gln Thr Ile Leu
1               5                   10                  15

Ser Lys Asp Leu Asn Ile Asp Gly Gly Gly Ser Gly Gly Gly Gly
            20                  25                  30

Ser Ser Gly Gln Thr Ile Lys Cys Val Val Gly Asp Gly Ala Val
        35                  40                  45

Gly Lys Thr Cys Leu Leu Ile Ser Tyr Thr Thr Asn Lys Phe Pro Ser
50                  55                  60

Glu Tyr Val Pro Thr Val Phe Asp Asn Tyr Ala Val Thr Val Met Ile
65                  70                  75                  80
```

```
Gly Gly Glu Pro Tyr Thr Leu Gly Leu Phe Asp Thr Ala Gly Gln Glu
                85                  90                  95

Asp Tyr Asp Arg Leu Arg Pro Leu Ser Tyr Pro Gln Thr Asp Val Phe
            100                 105                 110

Leu Val Cys Phe Ser Val Val Ser Pro Ser Ser Phe Glu Asn Val Lys
            115                 120                 125

Glu Lys Trp Val Pro Glu Ile Thr His His Cys Pro Lys Thr Pro Phe
            130                 135                 140

Leu Leu Val Gly Thr Gln Ile Asp Leu Arg Asp Asp Pro Ser Thr Ile
145                 150                 155                 160

Glu Lys Leu Ala Lys Asn Lys Gln Lys Pro Ile Thr Pro Glu Thr Ala
            165                 170                 175

Glu Lys Leu Ala Arg Asp Leu Lys Ala Val Lys Tyr Val Glu Cys Ser
            180                 185                 190

Ala Leu Thr Gln Lys Gly Leu Lys Asn Val Phe Asp Glu Ala Ile Leu
            195                 200                 205

Ala Ala Leu Glu Pro Pro Glu Pro Lys Lys Ser Arg Arg Cys Val Leu
            210                 215                 220

Leu
225

<210> SEQ ID NO 19
<211> LENGTH: 84
<212> TYPE: PRT
<213> ORGANISM: Artificial Sequence
<220> FEATURE:
<223> OTHER INFORMATION: Rac/Cdc42 (p21) binding domain (PBD) of the
      human p21 activated kinase 1 protein (PAK)-GFP11

<400> SEQUENCE: 19

Met Lys Glu Arg Pro Glu Ile Ser Leu Pro Ser Asp Phe Glu His Thr
1               5                   10                  15

Ile His Val Gly Phe Asp Ala Val Thr Gly Glu Phe Thr Gly Met Pro
            20                  25                  30

Glu Gln Trp Ala Arg Leu Leu Gln Thr Ser Asn Ile Thr Lys Ser Glu
            35                  40                  45

Gln Ile Asp Gly Gly Gly Ser Gly Gly Gly Ser Ser Gly Glu
        50                  55                  60

Lys Arg Asp His Met Val Leu Leu Glu Tyr Val Thr Ala Ala Gly Ile
65                  70                  75                  80

Thr Asp Ala Ser
```

METHODS FOR DETECTING PROTEIN-PROTEIN INTERACTIONS

FIELD OF THE INVENTION

The present invention relates to methods and kits for detection protein-protein interactions.

BACKGROUND OF THE INVENTION

Most cellular functions are driven by protein-protein interactions that regulate signal transduction and gene expression. Identifying partners involved in signaling pathways is of key importance in elucidating fundamentals of gene regulation mechanisms and in identifying aberrant cellular signaling processes occurring in various diseases. In recent years, a growing number of protein-based fluorescent biosensors have been developed to quantify and localize these interactions in living cells[1]. Fluorescence and Bioluminescence Resonance Energy transfer (FRET and BRET) based biosensors have emerged rapidly as they enable dynamic observations of protein-protein interactions[2]. Another class of reporters known as Protein-fragment Complementation Assay (PCA) has been developed to monitor direct interactions. These include split reporters from various enzymes, comprising the dihydrofolate reductase[3], the β-galactosidase[4], the β-lactamase[5], the firefly and Gaussia luciferases[6], Green Fluorescent Protein (GFP) variants[7], mostly known as Bimolecular Fluorescence Complementation (BiFC).

Luminescent biosensors based on split-luciferase (BiLC) have been widely validated for in vivo studies[8] and for high-throughput screening[9] (HTS) of small molecules and protein-protein interactions[10]. The method benefits from a great sensitivity due to the enzymatic activity of the luciferase reporter, but suffers from a lack of resolution for imaging subcellular structures. Fluorescent PCA, unlike luminescent proteins, are simply functional by the presence of a chromophore that is naturally activated by oxygen. This offers a great advantage as the method does not require extensive calibration and is particularly simple to implement by measurement of fluorescence. Fluorescent PCA have been described from fluorescent proteins originated from various species[11,12] and they still represent the reference method for protein complexes localization studies. Unlike Gaussia split luciferase[13], fluorescent based complementation assays are not reversible, but is advantageous for detecting low affinity or transient protein complexes[14], and facilitates the readout of complex formation. Most PCA are bimolecular components (two split reporter proteins), with a direct reporter activity correlated with complex formation. However, this scheme confers a great potential of false positive interactions due to spontaneous co-folding of split-proteins moieties. In a previous work, the inventors described a new method based on trimolecular split-GFP assay named "tripartite split-GFP technology" that exhibits very low background fluorescence and presents a highly specific readout of protein association[15].

SUMMARY OF THE INVENTION

The present invention relates to methods and kits for detection protein-protein interactions. In particular, the present invention is defined by the claims.

DETAILED DESCRIPTION OF THE INVENTION

In the present invention, the inventors have adapted the tripartite split-GFP assay to follow the activation of GTPases in living cells and have developed a new strategy to improve the sensitivity of the tripartite split-GFP method in cell based assays, particularly for the high throughput screening of protein-protein interactions and modulators of protein-protein interaction interfaces (activation/inhibition). In particular, the inventors developed a new assay for monitoring GTPase activation based on a tripartite split Green Fluorescent Protein (GFP)[23]. The split-GFP GTPase activation assay is composed of three fragments of the GFP: β-strand 10 fused to the GTPase, β-strand 11 fused to the GTPase Binding Domain (GBD) of an effector protein, and the large detector fragment β-strands 1 to 9 (GFP1-9). When the GTPase is activated it binds the GBD, which brings GFP10 and GFP11 close together to rapidly fuse with the GFP1-9 and reconstitute fluorescent full-length GFP. In this study, the inventors show that this biosensor system provides a direct measurement of small GTPase activation in vitro and in living cells. They further combine the tripartite split-GFP method with a specific GFP intrabody to obtain superior properties of this detection assay in vivo, combining fine analysis of GTPase localization studies and improved brightness of the biosensor for high content studies. This results in an increased sensitivity of the system for the detection in multi-well format, while preserving the specific assembly characteristics to robustly measure protein-protein interactions. Based on these findings, the inventors setup a cellular model to monitor and follow activation of RhoB GTPase, for which no FRET probe has been developed so far. The model highlights for the first time the visualization of RhoB activation visualized in different cellular contexts: serum starvation and stimulation with growth factors that lead to the reorganization of the endosomal and membrane pool of RhoB. The inventors show further that this cellular model is a robust and sensitive tool to study changes in RhoB activation profile in response to various stimulations, to the inhibition of GTPase regulators and upstream Rho GTPase signaling pathways. Together the results show that this strategy may be transposed to any protein-protein interaction and the screening of small-molecule and other factors that may modulate these interactions.

Accordingly, the present invention relates to methods for detecting the binding between a first polypeptide (A) and a second polypeptide (B) in a cell.

In some embodiments, the polypeptide (A) or (B) comprises at least 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; 190; 191; 192; 193; 194; 195; 196; 197; 198; 199; 200; 201; 202; 203; 204; 205; 206; 207; 208; 209; 210; 211; 212; 213; 214; 215; 216; 217; 218; 219; 220; 221; 222; 223; 224; 225; 226; 227; 228; 229; 230; 231; 232; 233; 234; 235; 236; 237; 238; 239; 240; 241; 242; 243; 244; 245; 246; 247; 248; 249; 250; 251; 252; 253; 254; 255; 256; 257; 258; 259; 260; 261; 262; 263; 264; 265; 266; 267; 268; 269; 270; 271; 272; 273; 274; 275; 276; 277; 278; 279; 280; 281; 282; 283; 284; 285; 286; 287; 288; 289; 290; 291; 292; 293; 294; 295; 296; 297; 298; 299; 300; 301; 302; 303; 304;

305; 306; 307; 308; 309; 310; 311; 312; 313; 314; 315; 316; 317; 318; 319; 320; 321; 322; 323; 324; 325; 326; 327; 328; 329; 330; 331; 332; 333; 334; 335; 336; 337; 338; 339; 340; 341; 342; 343; 344; 345; 346; 347; 348; 349; or 350; amino acids. For example, in some embodiments, the polypeptide includes a minimum length, such as at least 200 (such as at least 250, at least 300, at least 350, at least 400, at least 450, at least 500, at least 550, at least 600, at least 650, at least 700, at least 750, at least 800, at least 850, at least 900, at least 950, or at least 1000) amino acids in length.

In some embodiments, the polypeptide (A) or (B) represents a whole naturally occurring protein or fragment thereof.

In some embodiments, the polypeptide (A) is a GTPase and the polypeptide B is a GTPase binding domain (GBD). Small GTPases play an important role in signal transduction via transmembrane receptors to drive cytoplasmic or nuclear responses. They are involved in various fundamental cellular processes ranking from cytoskeleton organization to cell migration, and therefore are compelling pharmacological targets. In some embodiments, the GTPase belongs to the human Ras superfamily. The human Ras superfamily consists of 154 members divided in five main families: Ras, Rho, Rab, Arf and Ran. The Ras family is composed of three members H-Ras, K-Ras and N-Ras that are very closely related, with 85% amino acid sequence identity. Rho family proteins regroup small GTPases that contain a conserved Rho insert domain in the GTPase domain[16]. The leader members in the Rho subfamilies are RhoA, Rac1 and Cdc42 GTPases. Ras and Rho GTPases are molecular switches that cycle between GTP and GDP bound states. The activation state of Ras and Rho proteins depends on whether they are bound to GTP (active) or GDP (inactive). Binding to GTP is promoted by Rho Guanine nucleotide Exchange Factor (GEF), which promotes the GDP-GTP exchange, and GTP hydrolysis is catalyzed by GTPase Activating Protein (GAP) [17]. It is only in their active state (or GTP-bound) that Ras and Rho GTPases interact with a range of different effectors (E) to modulate their activity and localization[18]. As used herein the term "Rho-GTPase" has its general meaning in the art and refers to the Rho (ras homology) family of small molecular weight guanosine triphosphatases Rho GTPases are molecular switches that control signaling pathways regulating cytoskeleton organization, gene expression, cell cycle progression, cell motility and other cellular processes (Cell Communication and Signaling, 2010, 8, 23). Rho family GTPases are important signaling proteins that control diverse cellular functions related to cancer development, including actin cytoskeleton organization, transcription regulation, cell cycle progression, apoptosis, vesicle trafficking, and cell-to-cell and cell-to-extracellular matrix adhesions (Cell Communication and Signaling, 2010, 8 (23), 1-14; Genes Dev., 1997, 11, 2295-2322). In particular, Rho-GTPase includes RhoA, RhoB and RhoC. In some embodiments, the polypeptide (A) is an active or on active mutant of a GTPase.

In some embodiments, the present invention relates to a method for detecting the binding between a first polypeptide (A) and a second polypeptide (B) in a cell comprising:
i) providing a cell that expresses:
(a) a polypeptide (GFP1-9) comprising an amino acid sequence having at least 90% of identity with the amino acid sequence selected from the group consisting of SEQ ID NO:1-4
(b) a first fusion protein wherein the polypeptide (A) is fused to a polypeptide (GFP10) having an amino an amino acid sequence having at least 90% of identity with the amino acid sequence selected from the group consisting of SEQ ID NO:5-7

(c) a second fusion protein wherein the polypeptide (B) is fused to a polypeptide (GFP11) having an amino an amino acid sequence having at least 90% of identity with the amino acid sequence selected from the group consisting of SEQ ID NO:8-9
and (d) an intrabody specific for the complex formed by the self-assembly of the first, second and third polypeptides (a), (b) and (c)
ii) detecting the fluorescence wherein when the fluorescence is detected it is concluded that the polypeptide (A) binds to polypeptide (B) and where the fluorescence is not detected it is concluded that the polypeptides (A) does not bind to polypeptide (B).

In some embodiments, the GFP1-9 polypeptide consists of the amino acid sequence set forth in SEQ ID NO:1:

SEQ ID NO: 1: GFP1-9 OPT WT:
MRKGEELFTGVVPILIELDGDVNGHKFFVRGEGEGDATNGKLSLKFICTT

GKLPVPWPTLVTTLTYGVQCFSRYPDHMKRHDFFKSAMPEGYVQERTISF

KDDGTYKTRAEVKFEGDTLVNRIELKGIDFKEDGNILGHKLEYNFNSHNV

YITADKQKNGIKANFTIRHNVEDGSVQLADHYQQNTPIGDGPVLLP

In some embodiments, the GFP1-9 polypeptide consists of the amino acid sequence set forth in SEQ ID NO:2:

SEQ ID NO: 2: GFP1-9 OPT1
MRKGEELFTGVVPILIELDGDVNGHKFFVRGEGEGDATIGKLSLKFICTT

GKLPVPWPTLVTTLTYGVQCFSRYPDHMKRHDFFKSAMPEGYVQERTIYF

KDDGTYKTRAEVKFEGDTLVNRIELKGIDFKEDGNILGHKLEYNFNSHKV

YITADKQNNGIKANFTIRHNVEDGSVQLADHYQQNTPIGDGPVLLP

In some embodiments, the GFP1-9 polypeptide consists of the amino acid sequence set forth in SEQ ID NO:3:

SEQ ID NO: 3: GFP1-9 OPT2
MRKGEELFTGVVPILIELDGDVNGHKFFVRGEGEGDATIGKLSLKFICTT

GKLPVPWPTLVTTLTYGVQCFSRYPDHMKRHDFFKSAMPEGYVQERTIYF

KDDGTYKTRAEVKFEGDTLVNRIELKGIDFKEDGNILGHKLEYNFNPHNV

YITADKQKNGIKANFTIRHNVEDGSVQLAEHYQQNTPIGDGPVLLP

In some embodiments, the GFP1-9 polypeptide consists of the amino acid sequence set forth in SEQ ID NO:4:

SEQ ID NO: 4 GFP1-9 OPT3
MVRKGEELFTGVVPILIELDGDVNGHKFFVRGEGEGDATIGKLSLKFICT

TGKLPVPWPTLVTTLTYGVQCFSRYPDHMKRHDFFKSAMPEGYVQERTIY

FKDDGTYKTRAEVKFEGDTLVNRIELKGIDFKEDGNILGHKLEYNFNSHK

VYITADKQNNGIKANFTIRHNVEDGSVQLADHYQQNTPIGDPVD*

According to the invention a first amino acid sequence having at least 90% of identity with a second amino acid sequence means that the first sequence has 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet, 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

In some embodiments, the GFP1-9 polypeptide is fused to a subcellular targeting sequence of interest, such that the fragment is localized to the subcellular element of interest, following expression of the fragment in the cell or transfection into the cell. Therefore the assay can detect specifically protein-protein interactions in theses subcellular structures. Accordingly, non-imaging fluorescence detection can be used to determine if the cell has increased fluorescence, thereby indicating that the localization has occurred in the particular compartment to which the complementing fragments have been directed. If desired, imaging fluorescence microscopy is used to visualize the resulting, specifically-localized fluorescent signal, further confirming the presence of the test protein in the subcellular element of interest.

As used herein, the term "fusion protein" refers to the polypeptide (A) or (B) at least the heterologous detector polypeptide GFP10 or GFP11 respectively. In some embodiments, the fusion protein comprises the polypeptide (A) or (B) that is fused either directly or via a spacer at its C-terminal end to the N-terminal end of the heterologous detector polypeptide, or at its N-terminal end to the C-terminal end of the heterologous detector polypeptide. As used herein, the term "directly" means that the (first or last) amino acid at the terminal end (N or C-terminal end) of the polypeptide (A) or (B) is fused to the (first or last) amino acid at the terminal end (N or C-terminal end) of the heterologous detector polypeptide. In other words, in this embodiment, the last amino acid of the C-terminal end of said polypeptide is directly linked by a covalent bond to the first amino acid of the N-terminal end of said heterologous detector polypeptide, or the first amino acid of the N-terminal end of said polypeptide is directly linked by a covalent bond to the last amino acid of the C-terminal end of said heterologous detector polypeptide. As used herein, the term "spacer" refers to a sequence of at least one amino acid that links the polypeptide (A) or (B) to the heterologous detector polypeptide. Such a spacer may be useful to prevent steric hindrances. Suitable spacers are described herein and may— for example and without limitation—comprise an amino acid sequence, which amino acid sequence preferably has a length of 2 or more amino acids. Typically, the spacer has 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids. However, the upper limit is not critical but is chosen for reasons of convenience regarding e.g. biopharmaceutical production of such fusion proteins. The spacer sequence may be a naturally occurring sequence or a non-naturally occurring sequence. If used for therapeutical purposes, the spacer is preferably non-immunogenic in the subject to which the fusion protein of the present invention is administered. One useful group of spacer sequences are spacers derived from the hinge region of heavy chain antibodies as described in WO 96/34103 and WO 94/04678. Other examples are poly-alanine spacer sequences such as Ala-Ala-Ala. Further preferred examples of spacer sequences are Gly/Ser spacers of different length including (gly4ser)3, (gly4ser)4, (gly4ser), (gly3ser), gly3, and (gly3ser2)3.

In some embodiments, the GFP10 polypeptide consists of the amino acid sequence set forth in SEQ ID NO:5.

SEQ ID NO: 5
MGLPDNHYLSTQSVLSKDPN

In some embodiments, the GFP10 polypeptide consists of the amino acid sequence set forth in SEQ ID NO:6.

SEQ ID NO: 6
MDLPDNHYLSTQTILLKDLN

In some embodiments, the GFP10 polypeptide consists of the amino acid sequence set forth in SEQ ID NO:7.

SEQ ID NO: 7:
MDLPDDHYLSTQTILSKDLN

In some embodiments, the GFP11 polypeptide consists of the amino acid sequence set forth in SEQ ID NO:8.

SEQ ID NO: 8
EKRDHMVLLEFVTAAGITGAS

In some embodiments, the GFP11 polypeptide consists of the amino acid sequence set forth in SEQ ID NO:9.

SEQ ID NO: 9
EKRDHMVLLEYVTAAGITDAS

In some embodiments, the first fusion protein consists of the amino acid sequence set forth in SEQ ID NO:10, 11, 12, 13, 17 or 18.

GFP10-RhoA
SEQ ID NO: 10
MGDLPDDHYLSTQTILSKDLNIDGGGGSGGGGSSGAAIRKKLVIVGDGAC

GKTCLLIVFSKDQFPEVYVPTVFENYVADIEVDGKQVELALWDTAGQEDY

-continued
DRLRPLSYPDTDVILMCFSIDSPDSLXNIPXKWTPEVKHFCPNVPIILVG

NKKDLRNDEHTRRELAKMKQEPVKPEEGRDMANRIGAFGYMECSAKTKDG

VREVFEMATRAALQARRGKKKSGCLVL*

GFP10-RhoB

SEQ ID NO: 11
MGDLPDDHYLSTQTILSKDLNIDGGGGSGGGGSSGAAIRKKLVVVGDGAC

GKTCLLIVFSKDEFPEVYVPTVFENYVADIEVDGKQVELALWDTAGQEDY

DRLRPLSYPDTDVILMCFSVDSPDSLENIPEKWVPEVKHFCPNVPIILVA

NKKDLRSDEHVRTELARMKQEPVRTDDGRAMAVRIQAYDYLECSAKTKEG

VREVFETATRAALQKRYGSQNGCINCCKVL*

GFP10-HRas

SEQ ID NO: 12
MGDLPDDHYLSTQTILSKDLNIDGGGGSGGGGSSGTEYKLVVVGAGGVGK

NALTIQLIQNHFVDEYDPTIEDSYRKQVVIDGETCLLDILDTAGQEEYSA

MRDQYMRTGEGFLCVFAINNTKSFEDIHQYREQIKRVKDSDDVPMVLVGN

KCDLAARTVESRQAQDLARSYGIPYIETSAKTRQGVEDAFYTLVREIRQH

KLRKLNPPDESGPGCMSCKCVLS*

GFP10-NRas

SEQ ID NO: 13
MGDLPDDHYLSTQTILSKDLNIDGAGGSPGGGSGGSGSGGGGSGTEYKLV

VVGAGGVGKSALTIQLIQNHFVDEYDPTIEDSYRKQVVIDGETCLLDILD

TAGQEEYSAMRDQYMRTGEGFLCVFAINNSKSFADINLYREQIKRVKDSD

DVPMVLVGNKCDLPTRTVDTKQAHELAKSYGIPFIETSAKTRQGVEDAFY

TLVREIRQYRMKKLNSSDDGTQGCMGLPCVVM*

GFP10-Rac1

SEQ ID NO: 17
MGDLPDDHYLSTQTILSKDLNIDGGGGSGGGGSSGAIKCVVVGDGAVGKT

CLLISYTTNAFPGEYIPTVFDNYSANVMVDGKPVNLGLWDTAGQEDYDRL

RPLSYPQTDVFLICFSLVSPASFENVRAKWYPEVRHHCPNTPIILVGTKL

DLRDDKDTIEKLKEKKLTPITYPQGLAMAKEIGAVKYLECSALTQRGLKT

VFDEAIRAVLCPPPVKKRKRKCLLL*

GFP10-Cdc42

SEQ ID NO: 18
MGDLPDDHYLSTQTILSKDLNIDGGGGSGGGGSSGQTIKCVVVGDGAVGK

TCLLISYTTNKFPSEYVPTVFDNYAVTVMIGGEPYTLGLFDTAGQEDYDR

LRPLSYPQTDVFLVCFSVVSPSSFENVKEKWVPEITHHCPKTPFLLVGTQ

IDLRDDPSTIEKLAKNKQKPITPETAEKLARDLKAVKYVECSALTQKGLK

NVFDEAILAALEPPEPKKSRRCVLL

In some embodiments, the second fusion protein consists of the amino acid sequence set forth in SEQ ID NO: 14, 15 or 19.

Rho-binding domain of Rhotekin (RBD)-GFP11

SEQ ID NO: 14
MILEDLNMLYIRQMALSLEDTELQRKLDHEIRMRDGACKLLAACSQREQA
LEATKSLLVCNSRILSYMGELQRRKEAQVLEKTGIDGGGGSGGGGSSGEK
RDHMVLLEYVTAAGITDAS*

Ras binding domain of c-Raf (RsBD)-GFP11

SEQ ID NO: 15
MEHIQGAWKTISNGFGFKDAVFDGSSCISPTIVQQFGYQRRASDDGKLTD
PSKTSNTIRVFLPNKQRTVVNVRNGMSLHDCLMKALKVRGLQPECCAVFR
LLHEHKGKKARLDWNTDAASLIGEELQVDFLDHVPLTTHNFARKTFLKLG
IHRDIDGGGGSGGGGSSGEKRDHMVLLEYVTAAGITDAS*

SEQ ID NO: 19: Rac/Cdc42 (p21) binding domain (PBD) of the human p21 activated kinase 1 protein (PAK)-GFP11
MKERPEISLPSDFEHTIHVGFDAVTGEFTGMPEQWARLLQTSNITKSEQI
DGGGGSGGGGSSGEKRDHMVLLEYVTAAGITDAS As used the term "intrabody" has its general meaning in the art and refers to intracellularly expressed antibodies. Typically intrabodies are single chain antibodies and are typically selected from single chain Fv antibodies or single domain antibodies.

According to the invention, the intrabody binds to the reconstituted GFP when the complex is formed by the self-assembly of the first, second and third polypeptides (a), (b) and (c). The intrabody of the invention is not able to bind to the GFP1-9, GFP10 and GFP11 polypeptides by themselves.

As used herein, the term "single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in The Pharmacology of Monoclonal Antibodies, vol. 113, Rosenburg and Moore eds., (Springer-Verlag, New York, 1994), pp. 269-315.

As used herein, the term "single domain antibody" (sdAb) or "VHH" refers to the single heavy chain variable domain of antibodies of the type that can be found in Camelid mammals which are naturally devoid of light chains. According to the invention, sdAb can particularly be llama sdAb. The amino acid sequence and structure of a single domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1"; as "Complementarity Determining Region 2" or "CDR2" and as "Complementarity Determining Region 3" or "CDR3", respectively. Accordingly, the single domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single domain antibody are numbered according to the general numbering for VH domains given by the IMGT numbering system (Lefranc M.-P., "Unique database numbering system for immunogenetic analysis" Immunology Today, 18, 509 (1997)). The IMGT unique numbering has been defined to compare the variable domains whatever the antigen receptor, the chain type, or the species (Lefranc M.-P., "Unique database numbering system for immunogenetic analysis" Immunology Today, 18, 509 (1997); Lefranc M.-P., "The IMGT unique numbering for Immunoglobulins, T cell receptors and Ig-like domains" The Immunologist, 7, 132-

136 (1999); Lefranc, M.-P., Pommié, C., Ruiz, M., Giudicelli, V., Foulquier, E., Truong, L., Thouvenin-Contet, V. and Lefranc, G., "IMGT unique numbering for immunoglobulin and T cell receptor variable domains and Ig superfamily V-like domains" Dev. Comp. Immunol., 27, 55-77 (2003). In the IMGT unique numbering, the conserved amino acids always have the same position, for instance cysteine 23, tryptophan 41, hydrophobic amino acid 89, cysteine 104, phenylalanine or tryptophan 118. The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths become crucial information. Gaps in the CDR1-IMGT and CDR2-IMGT (less than 12 and 10 amino acid long, respectively) are put at the top of the CDR-IMGT loops. For instance, when the length of CDR1-IMGT is 7 amino acids, it comprises the positions 27, 28, 29, 30, 36, 37 and 38. When the length of CDR2-IMGT is 7 amino acids, it comprises the positions 56, 57, 58, 59, 63, 64, and 65. The basic length of a rearranged CDR3-IMGT is 13 amino acids (positions 105 to 117), which corresponds to a JUNCTION of 15 amino acids (2nd-CYS 104 to J-TRP or J-PHE 118). This length and corresponding numbering were chosen since they are convenient to use. Indeed, 80% of the IG and TR rearranged sequences in IMGT/LIGM-DB have a CDR3-IMGT length less than or equal to 13 amino acids. If the CDR3-IMGT length is less than 13 amino acids, gaps are created from the top of the loop, in the following order 111, 112, 110, 113, 109, 114, etc. Accordingly, when the length of CDR3-IMGT is 9 amino acids, it comprises the positions 105; 106; 107; 108; 109; 114; 115; 116; and 117. When length of CDR3-IMGT is 9 amino acids, it comprises the positions 105; 106; 107; 108; 109; 110; 112; 113; 114; 115; 116; and 117. If the CDR3-IMGT length is more than 13 amino acids, additional positions are created between positions 111 and 112 at the top of the CDR3-IMGT loop in the following order 112.1, 111.1, 112.2, 111.2, 112.3, 111.3, etc. Accordingly when the length of CDR3-IMGT is 15 amino acids, it comprises the additional positions 111.1 and 112.1.

The intrabody of the present invention may be prepared by starting with any of a variety of methods, including administering protein, fragments of protein, cells expressing the protein or fragments thereof and the like to an animal to induce polyclonal antibodies. The production of monoclonal antibodies is well known in the art. As detailed herein, such antibodies or antigen-binding fragments thereof may be used in the preparation of scFvs, VLS disulfide-free variants thereof and single domain antibodies. Additional steps in the production of antibodies of the invention include directed antibody evolution and affinity engineering. For example, the skilled person can obtain intrabodies that are able to bind to GFP protein and select those that are able to specifically recognize the complex formed by the self-assembly of the three split GFP domains, namely GFP1-9, GFP10 and GFP11.

In some embodiments, the single domain antibodies are disulfide-free antibodies. Typically, the intrabody of the present invention has a binding affinity (Kd) that in some embodiments, is between about 50 nM and about 5 nM. In some embodiments, the affinity of the intrabody of the present invention is about 10 nM. In some embodiments, the affinity of the intrabody is between about 5 nM and 3 nM. In some embodiments, the affinity of the intrabody is less than about 3 nM. In certain embodiments, the intrabody may have a Kd value greater than about 50 nM. The use of an antibody or antigen-binding fragment thereof of the invention that has a Kd value above about 50 nM, between about 50 nM and 5 nM, between about 5 nM and 3 nM, or below about 3 nM can be determined by one of ordinary skill in the art using art-known antibody activity assay methods.

In some embodiments, the intrabody of the present invention is a single domain antibody wherein
    the amino acid sequence of CDR1-IMGT has at least 90% of identity with the amino acid sequence ranging from the amino acid residue at position 29 to the amino acid residue at position 35 in SEQ ID NO:16
    the amino acid sequence of CDR1-IMGT has at least 90% of identity with the amino acid sequence ranging from the amino acid residue at position 54 to the amino acid residue at position 61 in SEQ ID NO:16
    the amino acid sequence of CDR1-IMGT has at least 90% of identity with the amino acid sequence ranging from the amino acid residue at position 101 to the amino acid residue at position 107 in SEQ ID NO:16
In some embodiments, the intrabody of the present invention is a single domain antibody comprising an amino acid sequence having at least 90% of identity with the amino acid sequence set forth in SEQ ID NO:16.

SEQ ID NO: 16: VHH
MDQVQLVESGGALVQPGGSLRLSCAASGFPVNRYSMRWYRQAPGKEREWV
AGMSSAGDRSSYEDSVKGRFTISRDDARNTVYLQMNSLKPEDTAVYYCNV
NVGFEYWGQGTQVTVSSAAAHHHHHHGAAEQKLISEEDLNGGSPG

In some embodiment, the intrabody is fused to a heterologous polypeptide to form fusion protein. In some embodiments, the heterologous polypeptide is a fluorescent polypeptide. Suitable fluorescent polypeptides include, but are not limited to, a green or red fluorescent protein (GFP or RFP), including, but not limited to, a "humanized" version of the FP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as Renilla reniformis, Renilla mulleri, or Ptilosarcus guernyi, as described in, e.g., WO 99/49019 and Peelle et al. (2001) J. Protein Chem. 20:507-519; "humanized" recombinant GFP (hrGFP) (Stratagene); any of a variety of fluorescent and colored proteins from Anthozoan species, as described in, e.g., Matz et al. (1999) Nature Biotechnol. 17:969-973; and the like (include RFP). In some embodiments, the heterologous polypeptide is an enzyme. Typically, said enzyme may be selected from the group consisting of β-galactosidase, alkaline phosphatase, luciferase, and horse radish peroxidise). Where the heterologous polypeptide is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc. In some embodiments, the heterologous polypeptide is a switchable domain, which can be activated by a small molecule or by photoactivation. Examples of small molecule switchable system include hormone ligand binding domain such as ERalpha LBD, Auxin AID system, HaloTag2 derivative system HyT or HALTS, FKB-FRB rapamycin or shieldl systems. Examples of photoactivation systems include Lov2 domain, PhyB-PIF, Cry2, UVR8, or Dronpa. These switchable systems are typically used for a precise spatial or temporal control of protein functions by conformational changed or relocalisation. In some embodiments, the heterologous polypeptide is tag so that the presence of the intrabody can be revealed by using an antibody specific for said tag. For example said tag may be selected from the group of myc-tag, FLAG-tag, T7-tag, HA (hemagglutinin)-tag, His-tag, S-tag, and GST-tag. Antibodies specific for said tags are commercially available.

In some embodiments, the intrabody of the present invention is conjugated with a detectable label. Suitable detectable labels include, for example, a radioisotope, a fluorescent label, a chemiluminescent label, an enzyme label, a bio luminescent label or colloidal gold. Methods of making and detecting such detectably-labeled immunoconjugates are well-known to those of ordinary skill in the art, and are described in more detail below. For instance, the detectable label can be a radioisotope that is detected by autoradiography. Isotopes that are particularly useful for the purpose of the present invention are 3H, 125I, 131I, 35S and 14C. The intrabody (fused or not to the heterologous polypeptide) can also be labeled with a fluorescent compound. The presence of a fluorescently-labeled single domain antibody of the present invention is determined by exposing the immuno conjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine and Alexa Fluor dyes. Alternatively, the intrabody can be detectably labeled by coupling said single domain antibody to a chemiluminescent compound. The presence of the chemiluminescent-tagged immuno conjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester. Similarly, a bio luminescent compound can be used to label the intrabody. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin. Typically, when the single domain antibody is fused to a fluorescent polypeptide as described above, the presence of the fusion protein can be detected with any means well known in the art such as a microscope or microscope or automated analysis system. Typically, when the single domain antibody is fused to an enzyme then, the fusion protein is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase. Those of skill in the art will know of other suitable labels which can be employed in accordance with the present invention. The binding of marker moieties to anti-the intrabody is accomplished using standard techniques known to the art. Typical methodology in this regard is described by Kennedy et al., Clin. Chim. Acta 70: 1, 1976; Schurs et al., Clin. Chim. Acta 81: 1, 1977; Shih et al., Int'U. Cancer 46: 1101, 1990; Stein et al, Cancer Res. 50: 1330, 1990; and Coligan, supra. Moreover, the convenience and versatility of immunochemical detection can be enhanced by using single domain antibodies of the present invention (fused or not to the heterologous polypeptide) that have been conjugated with avidin, streptavidin, and biotin. {See, e.g., Wilchek et al. (eds.), "Avidin-Biotin Technology," Methods In Enzymology (Vol. 184) (Academic Press 1990); Bayer et al., "Immunochemical Applications of Avidin-Biotin Technology," in Methods In Molecular Biology (Vol. 10) 149-162 (Manson, ed., The Humana Press, Inc. 1992).) In some embodiments, the presence of the single domain antibody (fused or not to the heterologous polypeptide) is detected with a secondary antibody that is specific for the single antibody of the present invention (fused or not to the heterologous polypeptide). Typically said secondary is labeled by same methods as described above. For instance when the intrabody is fused to a tag (e.g. histidine tag) the secondary antibody is specific for said tag. Methods for performing immunoassays are well-established. {See, e.g., Cook and Self, "Monoclonal Antibodies in Diagnostic Immunoassays," in Monoclonal Antibodies: Production, Engineering, and Clinical Application 180-208 (Ritter and Ladyman, eds., Cambridge University Press 1995); Perry, "The Role of Monoclonal Antibodies in the Advancement of Immunoassay Technology," in Monoclonal Antibodies: Principles and Applications 107-120 (Birch and Lennox, eds., Wiley-Liss, Inc. 1995); Diamandis, Immunoassay (Academic Press, Inc. 1996).)

Typically, the cell of step i) is obtained by transforming a host cell by a plurality of nucleic acids encoding for the polypeptides (a), (b), (c) and (d).

As used herein, the term "nucleic acid molecule" has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fiuorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term "transformation" means the introduction of a "foreign" (i.e. extrinsic or extracellular) nucleic acid to a host cell, so that the host cell will express the introduced nucleic acid to produce the desired polypeptide of the invention (i.e. polypeptides (a), (b), (c), and (d). A host cell that receives and expresses the introduced nucleic acid has been "transformed".

In some embodiments, the host is a prokaryotic cell and, in particular E. coli cell, In some embodiments, the host cell is an eukaryotic cell (e.g. yeast, mammalian cell). In some embodiments, the host cells is isolated from a mammalian subject who is selected from a group consisting of: a human, a horse, a dog, a cat, a mouse, a rat, a cow and a sheep. In some embodiments, the host cell is a human cell. In some embodiments, the host cell is a cell in culture. The cells may be obtained directly from a mammal (preferably human), or from a commercial source, or from tissue, or in the form for instance of cultured cells, prepared on site or purchased from a commercial cell source and the like. The cells may come from any organ including but not limited to the blood or lymph system, from muscles, any organ, gland, the skin, brain, lung . . . . In some embodiments, the cells are selected from the group consisting of epithelial cells, neural cells, epidermal cells, keratinocytes, hematopoietic cells, melanocytes, chondrocytes, hepatocytes, B-cells, T-cells, erythrocytes, macrophages, monocytes, fibroblasts, muscle cells, vascular smooth muscle cells, hepatocytes, splenocytes, pancreatic beta cells . . . . In some embodiments, the host cell is a cancer cell. Typically, the cancer cells are isolated from a cancer selected from the group consisting of breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiment, the host cells is a stem cell. As used herein, the term "stem cell" refers to an undifferentiated cell that can be induced to proliferate. The stem cell is capable of self-maintenance or self-renewal, meaning that with each cell division, one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type. Stem cells include pluripotent stem cells, which can form cells of any of the body's tissue lineages: mesoderm, endoderm and ectoderm. Therefore, for example, stem cells can be selected from a human embryonic stem (ES) cell; a human inner cell mass (ICM)/epiblast cell; a human primitive ectoderm cell, a human primitive endoderm cell; a human primitive mesoderm cell; and a human primordial germ (EG) cell. Stem cells also include multipotent stem cells, which can form multiple cell lineages that constitute an entire tissue or tissues, such as but not limited to hematopoietic stem cells or neural precursor cells. Stem cells also include totipotent stem cells, which can form an entire organism. In some embodiment, the stem cell is a mesenchymal stem cell. The term "mesenchymal stem cell" or "MSC" is used interchangeably for adult cells which are not terminally differentiated, which can divide to yield cells that are either stem cells, or which, irreversibly differentiate to give rise to cells of a mesenchymal cell lineage, e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. In some embodiments, the stem cell is a partially differentiated or differentiating cell. In some embodiments, the stem cell is an induced pluripotent stem cell (iPSC), which has been reprogrammed or de-differentiated. Stem cells can be obtained from embryonic, fetal or adult tissues.

In some embodiments, the nucleic acid molecule is included in a suitable vector for transforming the host cell, such as a plasmid, cosmid, episome, artificial chromosome, phage or a viral vector. Typically, the vector is a viral vector which is an adeno-associated virus (AAV), a retrovirus, bovine papilloma virus, an adenovirus vector, a lentiviral vector, a vaccinia virus, a polyoma virus, or an infective virus. Retroviruses may be chosen as gene delivery vectors due to their ability to integrate their genes into the host genome, transferring a large amount of foreign genetic material, infecting a broad spectrum of species and cell types and for being packaged in special cell-lines. In order to construct a retroviral vector, a nucleic acid encoding a gene of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV 1, HIV 2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are known in the art, see, e.g. U.S. Pat. Nos. 6,013,516 and 5,994,136, both of which are incorporated herein by reference. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest. Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species. Typically, the nucleic acid molecule or the vector of the present invention include "control sequences", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Another nucleic acid sequence, is a "promoter" sequence, which is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

In some embodiments, the cell of step i) is prepared by from a pre-established cell line that is already transformed by a nucleic acid encoding the polypeptide (GFP1-9) of the present invention and a nucleic acid encoding for the intrabody of the present invention. Accordingly, when the polypeptides (A) and (B) are selected, the cell line is thus further transformed with the first and second fusion protein of the present invention to prepare the cell of step i).

According a further object of the present invention relates to a host cell that expresses i) a polypeptide (GFP1-9) comprising an amino acid sequence having at least 90% of identity with the amino acid sequence selected from the group consisting of SEQ ID NO:1-4, and ii) the intrabody of the present invention.

A further object of the present invention relates to a host cell that expresses i) a polypeptide (GFP1-9) comprising an amino acid sequence having at least 90% of identity with the amino acid sequence selected from the group consisting of SEQ ID NO:1-4, ii) a first fusion protein wherein the polypeptide (A) is fused to a polypeptide (GFP10) having an amino an amino acid sequence having at least 90% of identity with the amino acid sequence selected from the group consisting of SEQ ID NO:5-7, iii) a second fusion protein wherein the polypeptide (B) is fused to a polypeptide (GFP11) having an amino an amino acid sequence having at least 90% of identity with the amino acid sequence selected from the group consisting of SEQ ID NO:8-9 and iv) an intrabody specific for the complex formed by the self-assembly of the first, second and third polypeptides i), ii) and iii).

With respect to the detection of fluorescence, any well-known methods and devices can be used. Typically the cells emit a specific fluorescence (e.g. green fluorescence) by exposing to excitation light. The cell is indeed illuminated with a wavelength of light selected to give a detectable optical response, and observed with a means for detecting the optical response. Equipment that is useful for illuminating the fluorescent compounds of the present invention includes, but is not limited to, hand-held ultraviolet lamps, mercury arc lamps, xenon lamps, lasers and laser diodes. These illumination sources are optically integrated into laser scanners, fluorescent microplate readers or standard or microfluorometers. The optical response is optionally detected by visual inspection, or by use of any of the following devices: CCD camera, video camera, photographic film, laser-scanning devices, fluorometers, photodiodes, quantum counters, epifluorescencea microscopes, scanning microscopes, flow cytometers, fluorescence microplate readers, or by means for amplifying the signal such as photomultiplier tubes. Where the sample is examined using a flow cytometer, examination optionally includes sorting portions of the sample according to their fluorescence response. In some embodiments, the cells are observed under fluorescence microscope. Confocal microscopy is typically used. In some embodiments, expression of GFP fluorescence may be observed with a CCD camera. In some embodiments detection of fluorescence uses a CCD camera or CMOS imaging device. In some embodiments, fluorescence is detected by using an automated instrument that sorts cells according to the detectable fluorescence response, such as by fluorescence activated cell sorting (FACS).

In some embodiments, when the intrabody of the present invention is labelled with a detectable molecule, co-localization of the emitting signals is thus indicative of that the polypeptide (A) binds to the polypeptide (B). The time and spatial resolution can thus be optimized when the intrabody of the present invention is labelled with a detectable molecule.

In some embodiments, the detecting method of the present invention further comprises determining the subcellular localization of the emitted fluorescence. As used herein the term "subcellular localization" refers to the location of the detected fluorescence in relation to a subcellular compartment. For example, a subcellular compartment may be an organelle within a cell, a membrane within a cell or an area surrounding a particular structure of a cell. Examples of subcellular compartments within eukaryotic cells include cytoplasm, nucleus, mitochondria, Golgi apparatus, endoplasmic reticulum (ER), peroxisome, lysosomes, endosomes (early, intermediate, late, etc.), vacuoles, cytoskeleton, nucleoplasm, nucleolus, nuclear matrix and ribosomes. In some embodiments, a subcellular compartment can be defines by proximity to a particular location within a cell, for example, the post-synaptic density of a neuron. See, e.g., Alberts et al., Molecular Biology of the Cell, 5thedition, New York, Garland Science, 2005.

A distinct advantage of the detecting method of the present invention is the absence of background fluorescence prior to complementation. Only if complementation occurs in a particular compartment to which one or more protein complexes are formed, does that compartment become fluorescent. It is necessary only to measure the fluorescence of the cell to determine whether the specific protein-protein interaction has occurred, enabling high-throughput screens using flow cytometry, for example, without the need to specifically visualize all the structures in the cell by microscopy.

The detecting method of the present invention is thus particularly suitable for performing screening methods for identifying candidate compounds that are able to modulate (i.e. decrease or increase) the binding between the polypeptides (A) and (B).

Accordingly, a further object of the present invention relates to a method for screening a compound capable of modulating (i.e. increasing or decreasing) the binding between a polypeptide (A) and a polypeptide (B) comprising the step of i) providing a cell that expresses:
(a) a polypeptide (GFP1-9) comprising an amino acid sequence having at least 90% of identity with the amino acid sequence selected from the group consisting of SEQ ID NO:1-4
(b) a first fusion protein wherein the polypeptide (A) is fused to a polypeptide (GFP10) having an amino an amino acid sequence having at least 90% of identity with the amino acid sequence selected from the group consisting of SEQ ID NO:5-7
(c) a second fusion protein wherein the polypeptide (B) is fused to a polypeptide (GFP11) having an amino an amino acid sequence having at least 90% of identity with the amino acid sequence selected from the group consisting of SEQ ID NO:8-9
and (d) an intrabody specific for the complex formed by the self-assembly of the first, second and third polypeptides (a), (b) and (c)
ii) contacting the cell with a candidate compound,
iii) detecting the fluorescence
iii) positively selecting the candidate compound when the fluorescence is modulated In some embodiments, the screening method further comprises a step of comparing the fluorescence detection with the one obtained in the absence of the candidate compound. Typically, when the fluorescence is detected in the presence of the candidate compound then it is concluded that the candidate compound positively modulates (i.e. enhances) the binding between polypeptide (A) and polypeptide (B). Typically, when the fluorescence is not detected in the presence of the candidate compound then it is concluded that the candidate compound negatively modulates (i.e. decreases or inhibit) the binding between polypeptide (A) and polypeptide (B). Accordingly, detecting the fluorescence (or lack thereof) can thus include detecting an increase (or decrease) in fluorescence compared to a standard value. As used herein, the term "standard value" refers to a negative or positive control value. The standard value provides a control value against which the detected fluorescence in the presence of a candidate compound can be compared. Standard values can be easily determined by those skilled in the art and tailored to suit the particular requirements of the experiments performed. Usually, a plurality of samples are prepared, so as to add increasing amounts of the candidate compound to be tested in distinct samples. Generally, at least one sample without candidate compound is also prepared as a negative control for further comparison. In some embodiments, a control sample is prepared with a compounds known to positively or negatively modulate the binding between the polypeptides (A) and (B).

Candidate compounds employed in the screening methods of this invention include for example, without limitation, synthetic organic compounds, chemical compounds, naturally occurring products, polypeptides and peptides, nucleic acids, etc.

Essentially any chemical compound can be used as a potential candidate compound. Most often compounds dissolved in aqueous or organic (especially dimethyl sulfoxide- or DMSO-based) solutions are used. The assays are designed to screen large chemical libraries by automating the assay steps. The compounds are provided from any convenient source to the cells. The assays are typically run in parallel (e.g., in microtiter formats on microtiter plates in robotic assays with different candidate compounds in different wells on the same plate). It will be appreciated that there are many suppliers of chemical compounds, including ChemDiv (San Diego, Calif.), Sigma-Aldrich (St. Louis, Mo.), Fluka Chemika-Biochemica-Analytika (Buchs Switzerland) and the like. In some embodiments, the screening method involves providing a small organic molecule or peptide library. Such "chemical libraries" are then screened in one or more assays, as described herein, to identify those library members (particular chemical species or subclasses) that display a desired characteristic activity. The compounds thus identified can serve as conventional "lead compounds" or can themselves be used as potential or actual products. A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks. Preparation and screening of combinatorial chemical libraries is well known to those of skill in the art. Such combinatorial chemical libraries include, but are not limited to, peptide libraries (see, e.g., U.S. Pat. No. 5,010,175; Furka Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14:309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Asinex, Moscow, Russia; Tripos, Inc., St. Louis, Mo.; ChemStar, Ltd, Moscow, Russia; 3D Pharmaceuticals, Exton, Pa.; Martek Biosciences, Columbia, Md.; etc.). Candidate compounds encompass numerous chemical classes, though typically they are organic molecules, preferably small organic compounds having a molecular weight of more than 100 and less than about 10,000 daltons, preferably, less than about 2000 to 5000 daltons. Candidate compounds may comprise functional groups necessary for structural interaction with proteins, particularly hydrogen bonding, and typically include at least an amine, carbonyl, hydroxyl or carboxyl group, preferably at least two of the functional chemical groups. The candidate compounds may comprise cyclical carbon or heterocyclic structures, and/or aromatic or polyaromatic structures substituted with one or more of the above functional groups. Candidate compounds are also found among biomolecules including peptides, saccharides, fatty acids, steroids, purines, pyrimidines, derivatives, structural analogs or combinations thereof.

In some embodiments, the screening method of the present invention is particularly suitable for screening upstream modulators of the binding between the polypeptide (A) and the polypeptide (B). Actually, the candidate compound may indirectly modulate the binding between the 2 polypeptides (A) and (B) by interacting with an upstream component that will then modulate the binding. For example, focused kinase inhibitor compound libraries may be used to provide the candidate compounds. Thus, the candidate compound may be a compound already identified as a protein kinase inhibitor. These may be used to identify compound 'hits' (typically non-selective, low potency chemical start points). Available sequence knowledge, structural predictions and known kinase ligands may also be used to virtually screen commercially available compounds for novel compound hits. In some embodiments, the candidate compounds may inhibit or down-regulate the expression of a particular host cell gene, including coding and non coding sequence (e.g. miRNA). Such candidate compounds may comprise nucleic acid for example, oligonucleotide sequences, specifically designed to inhibit the expression of one or more host cell sequences—. Suitable candidate compounds may include, for example, DNA or RNA oligonucleotides, preferably antisense oligonucleotides. Such siRNA oligonucleotides may take the form of single or double-stranded RNA molecules which have been modified in some way (for example by chemical modification) to be nuclease resistant. In order to decrease or down-regulate the expression of a particular host cell sequence, or to block the activity of the host cell sequence (e.g. miRNA), the host cell may be contacted or transfected with any of the abovementioned candidate compounds. By analysing native or wild-type host cell sequences and with the aid of algorithms such as BIO-PREDsi, one of skill in the art could easily determine or computationally predict nucleic acid sequences that have an optimal knockdown effect for these genes (see for example: http://www.biopredsi.org/start.html). Accordingly, the skilled man may generate and test an array or library of different oligonucleotides to determine whether or not they are capable of modulating the expression, function and/or activity of certain host cell sequence.

A variety of other reagents may be included in the screening assay according to the present invention. Such reagents include, but are not limited to, salts, solvents, neutral proteins, e.g. albumin, detergents, etc., which may be used to facilitate optimal protein-protein binding and/or to reduce non-specific or background interactions. Examples of solvents include, but are not limited to, dimethyl sulfoxide (DMSO), ethanol and acetone, and are generally used at a concentration of less than or equal to 1% (v/v) of the total assay volume. In addition, reagents that otherwise improve the efficiency of the assay, such as protease inhibitors, anti-microbial agents, etc. may be used. Further, the mixture of components in the method may be added in any order that provides for the requisite binding.

Typically, the screening method of the present invention is performed in a multi-well format. By "well" it is meant generally a bounded area within a container, which may be either discrete (e.g., to provide for an isolated sample) or in communication with one or more other bounded areas (e.g., to provide for fluid communication between one or more samples in a well). For example, cells grown on a substrate are normally contained within a well that may also contain culture medium for living cells. Substrates can comprise any suitable material, such as plastic, glass, and the like. Plastic is conventionally used for maintenance and/or growth of cells in vitro. A "multi-well vessel", as noted above, is an example of a substrate comprising more than one well in an array. Multi-well vessels useful in the invention can be of any of a variety of standard formats (e.g., plates having 2, 4, 6, 24, 96, 384, or 1536, etc., wells), but can also be in a non-standard format (e.g., plates having 3, 5, 7, etc., wells). When the assays of the invention are performed in a multi-well format, a suitable device for detecting changes in fluorescence used is a multi-well microplate reader. Suitable devices are commercially available, for example, from Molecular Devices (FLEXstation® microplate reader and fluid transfer system or FLIPR® system), from Hamamatsu (FDSS 6000) and the "VIPR" voltage ion probe reader (Aurora, Bioscience Corp. Calif., USA). The FLIPR-Tetra™ is a second generation reader that provides real-time kinetic cell-based assays using up to 1536 simultaneous liquid transfer systems. All of these systems can be used with commercially available dyes such as FMP, which excites in the visible wavelength range. Using the FLIPR® system, the change in fluorescent intensity is monitored over time and is graphically displayed. Several commercial fluorescence detectors are available that can inject liquid into a single well or simultaneously into multiple wells. These include, but are not limited to, the Molecular Devices FlexStation (eight wells), BMG NovoStar (two wells) and Aurora VIPR (eight wells). Typically, these instruments require 12 to 96 minutes to read a 96-well plate in flash luminescence or fluorescence mode (1 min/well). An alternative method is to inject the modulator into all sample wells at the same time and measure the luminescence in the whole plate by imaging with a charge-coupled device (CCD) camera, similar to the way that calcium responses are read by calcium-sensitive fluorescent dyes in the FLIPR®, FLIPR-384 or FLIPR-Tetra™ instruments. Other fluorescence imaging systems with integrated liquid handling are expected from other commercial suppliers such as the second generation LEAD-SEEKER from Amersham, the Perkin Elmer CellLux-Cellular Fluorescence Workstation and the Hamamatsu FDSS6000 System. These instruments can generally be configured to proper excitation and emission settings to read.

In some embodiments, the screening method of the present invention is performed in a high throughput screening assay. High-throughput screening (HTS) assays are typically used in drug discovery. Using robotics, data processing and control software, liquid handling devices, and sensitive detectors, High-throughput screening allows a quickly conduct millions of chemical, genetic, or pharmacological tests. Through this process one can rapidly identify the candidate compounds capable of modulating the binding between polypeptides (A) and (B).

A further object of the present invention relates to a kit suitable for performing one method of the present invention (i.e. detecting or screening method of the present invention). Kits thus contain various materials and reagents (e.g., for practicing the methods described herein). For example, a kit may contain reagents including, without limitation, polypeptides or polynucleotides, cell transformation and transfection reagents, reagents and materials for purifying polynucleotides and polypeptides including lysis regents, protein denaturing and refolding reagents, as well as other solutions or buffers useful in carrying out the assays and other methods of the invention. Kits may also include control samples, materials useful in calibrating methods described herein, and containers, tubes, microtiter plates and the like in which assay reactions may be conducted. Kits may be packaged in containers, which may comprise compartments for receiving the contents of the kits, instructions for conducting methods described herein or using the polypeptides and polynucleotides described herein, etc. For example, a kit of the present invention provides one or more polypeptides as described herein, one or more polynucleotide constructs encoding the one or more polypeptides, cell strains suitable for propagating the constructs, cells pre-transformed or stably transfected with constructs encoding one or more polypeptides, and reagents for purification of expressed fusion proteins or nucleotide encoding an expressed fusion protein. In some embodiments, the kit comprise a plurality of cells according to the present invention in particular an amount of cells that express i) a polypeptide (GFP1-9) comprising an amino acid sequence having at least 90% of identity with the amino acid sequence selected from the group consisting of SEQ ID NO:1-4, and ii) the intrabody of the present invention. In some embodiments the kits comprises means for determining the subcellular localization of the protein-protein interaction as described herein. The kit can include a container and a label or package insert on or associated with the container. The label or package insert typically will further include instructions for use of the polypeptide, nucleic acid molecules, or expression vector provided with the kit, for example for use in the methods disclosed herein. The instructional materials may be written, in an electronic form (such as a computer diskette or compact disk) or may be visual (such as video files).

The invention will be further illustrated by the following figures and examples. However, these examples and figures should not be interpreted in any way as limiting the scope of the present invention.

FIGURES

FIG. 1: Tripartite split-GFP complementation is correlated with GTPase activity. a) In this assay, the two single GFP β-strands GFP10 and GFP11 are respectively fused to the GTPase and its GTPase binding domain (GBD) and co-transfected in HEK cells expressing stably the GFP1-9 detector fragment. When the GTPase is activated, the GTP-bound form of the GTPase binds to the GBD, which allows tripartite GFP complementation and fluorescence emission. Conversely, if the GTPase is inactive (bound to GDP), the interaction does not occur and no fluorescent signal is emitted. b) Western blot analysis of GST-RBD pulldown of GFP10-RhoA and GFP10-RhoB chimera (wild-type, Q63L, T19N) transfected into HEK1_9 cells. Total Rho and beads-bound active Rho (Rho-GTP) were detected with anti-RhoA or anti-RhoB antibodies. c)c')c") Flow cytometry analysis of tripartite split-GFP complementation assays for various GFP10-GTPase fusions: dominant negative variants of RhoA, RhoB (T19N) and H-Ras (S17N), and dominant positive variants of RhoA, RhoB (Q63L) and H-Ras (G12V) with the Rho-binding domain of Rhotekin (RBD) and/or the Ras binding domain of c-Rafl (RsBD) tagged with GFP11 (n=3; mean+/−SEM). Expression of the corresponding protein chimera is controlled by western blot analysis of the same cell extracts revealed with anti-Rho antibodies and with immune rabbit serum against the GFP11 peptide. d)d')d") Representative graphs of FL1-H/SSC-H cytograms and their respective mean fluorescence intensity values.

Figure 2:
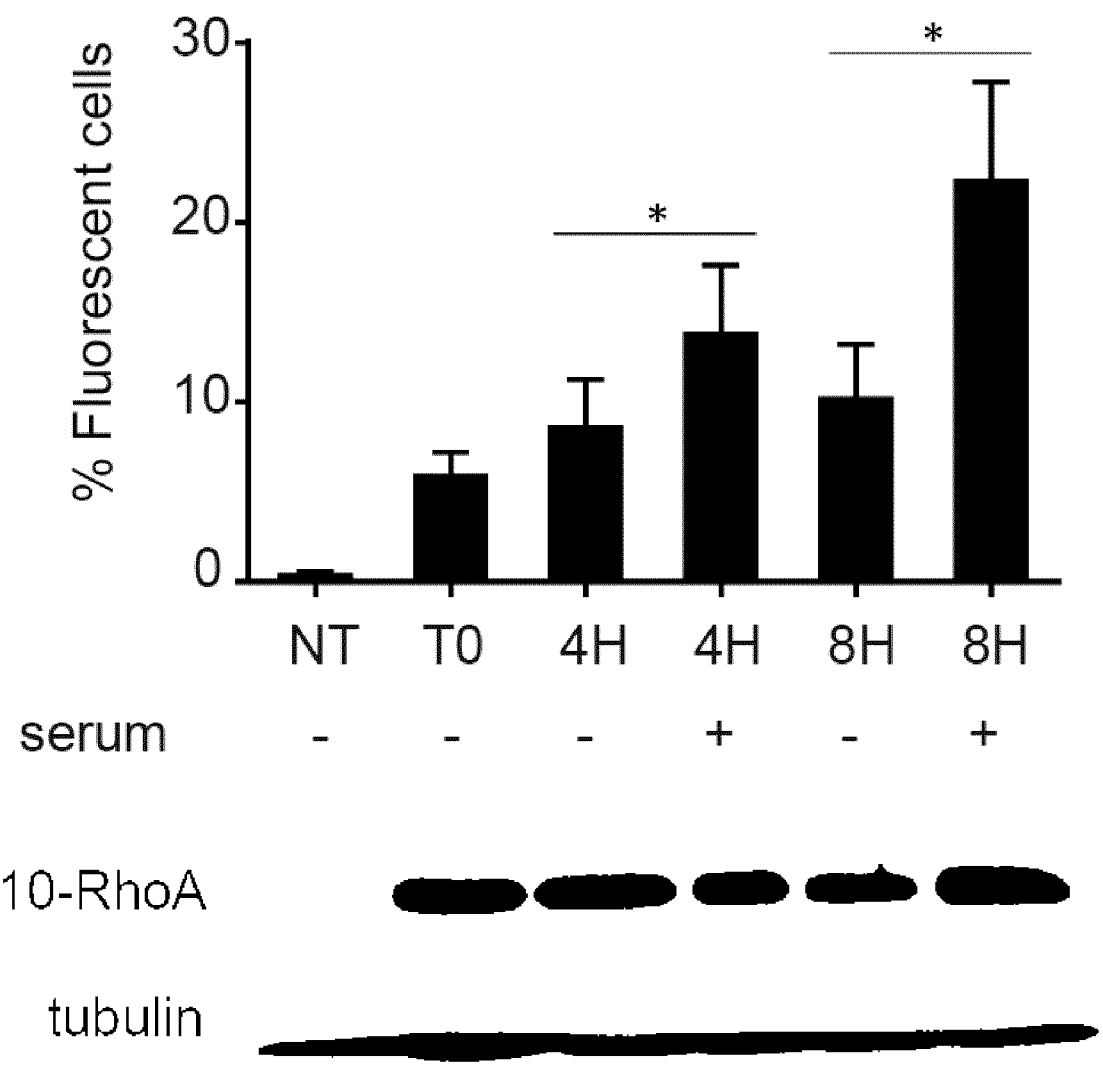

FIG. 2: Activation of wild-type RhoA with growth factors. Flow cytometry analysis of tripartite split-GFP complementation in HEK_GFP1-9 cells co-expressing wild-type RhoA fused to GFP10 and the Rho binding domain (RBD) fused to GFP11. After 48 H of serum-starvation (T0), cells were stimulated with 10% FBS and the percentage of fluorescent cells was measured at different times (4H and 8H). The statistical significance between stimulated and unstimulated cells was assessed using a paired Student's t-test (*p<0.05).

Figure 3:
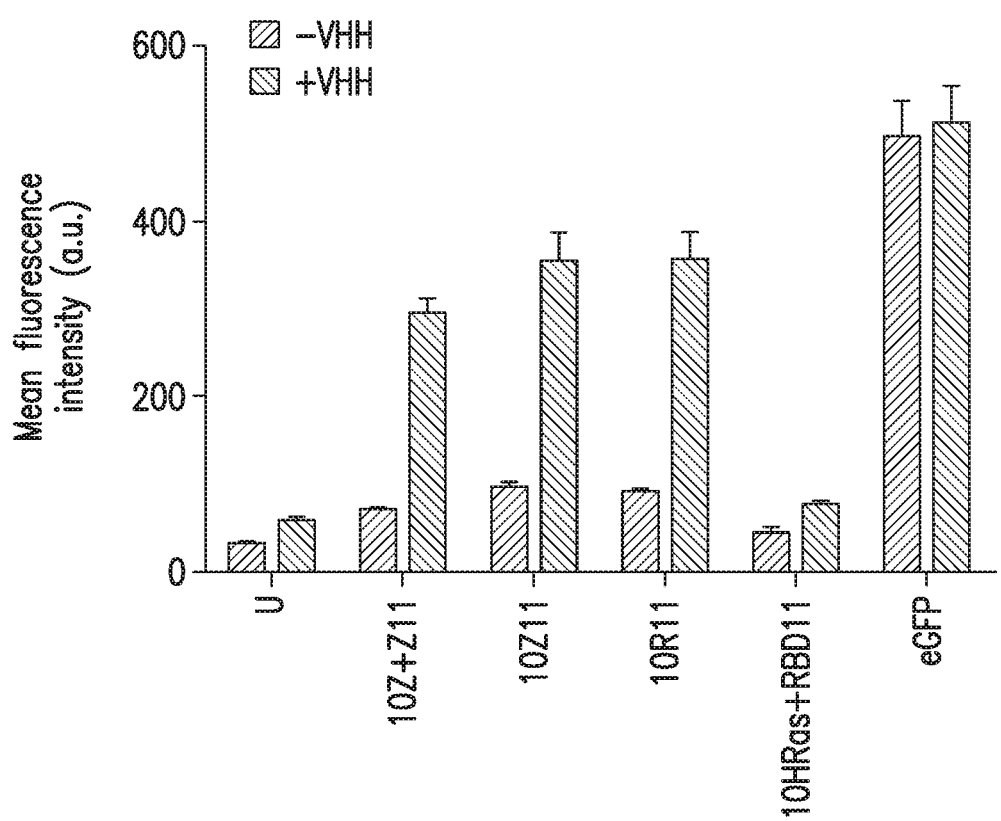

FIG. 3: Effect of binding of anti-GFP VHH nanobody to the reconstituted split-GFP. Effect of the anti-GFP VHH nanobody on the reconstituted split-GFP fluorescence intensity. Several GFP1-9 self-interacting domains (10-R-11, 10-zipper-11); the leucine zipper heterodimer (10Z/Z11) and the non-interacting protein pair 10-HRas/RBD-11 were transfected in MRCS SV_GFP1-9 cells and analyzed for split-GFP complementation with or without anti-GFP VHH. Full-length eGFP was used as a control. After 24 H, the mean fluorescence intensity was analyzed by flow cytometry (n=3; mean+/−SEM).

EXAMPLE

Introduction:

Small GTPases play an important role in signal transduction via transmembrane receptors to drive cytoplasmic or nuclear responses. They are involved in various fundamental cellular processes ranking from cytoskeleton organization to cell migration, and therefore are compelling pharmacological targets. The human Ras superfamily consists of 154 members divided in five main families: Ras, Rho, Rab, Arf and Ran. The Ras family is composed of three members H-Ras, K-Ras and N-Ras that are very closely related, with 85% amino acid sequence identity. Rho family proteins regroup small GTPases that contain a conserved Rho insert domain in the GTPase domain[16]. The leader members in the Rho subfamilies are RhoA, Rac1 and Cdc42 GTPases. Ras and Rho GTPases are molecular switches that cycle between GTP and GDP bound states. The activation state of Ras and Rho proteins depends on whether they are bound to GTP (active) or GDP (inactive). Binding to GTP is promoted by Rho Guanine nucleotide Exchange Factor (GEF), which promotes the GDP-GTP exchange, and GTP hydrolysis is catalyzed by GTPase Activating Protein (GAP)[17]. It is only in their active state (or GTP-bound) that Ras and Rho GTPases interact with a range of different effectors (E) to modulate their activity and localization[18].

Signaling of small GTPases is complex and involves interactions between several protein partners, which is strongly dependent on their subcellular localization. Live cell assays for monitoring GTPase activation have highlighted for the first time the spatiotemporal activity of GTPases in living cells. Various specific Fluorescence Resonance Energy Transfer (FRET) probes have specifically been engineered for the major members of Ras superfamily such as RhoA, Rac1, Cdc42 and Ras to report GTPase activities in migrating cells[19-22]. This approach offers a dynamic view of such signaling and enables to follow a fine-tuning of GTPase activation at high spatiotemporal resolution. However, these assays are not suitable for studying multiple protein-protein interactions or screening large small molecules libraries. At present, novel methods are needed for analyzing Ras and Rho protein interactions in their natural environment with a higher throughput.

Here, we developed a new assay for monitoring GTPase activation based on a tripartite split Green Fluorescent Protein (GFP)[23]. The split-GFP GTPase activation assay is composed of three fragments of the GFP: β-strand 10 fused to the GTPase, β-strand 11 fused to the GTPase Binding Domain (GBD) of an effector protein, and the large detector fragment β-strands 1 to 9 (GFP1-9). When the GTPase is activated it binds the GBD, which brings GFP10 and GFP11 close together to rapidly fuse with the GFP1-9 and reconstitute fluorescent full-length GFP. In this study, we show that this biosensor system provides a direct measurement of small GTPase activation in vitro and in living cells. We further combine the tripartite split-GFP method with specific a GFP intrabody to obtain superior properties of this detection assay in vivo, combining fine analysis of GTPase localization studies and improved brightness of the biosensor for high content studies. This results in an increased sensitivity of our system for the detection in multi-well format, while preserving the specific assembly characteristics to robustly measure protein-protein interactions. Based on these findings, we setup a cellular model to monitor and follow activation of RhoB GTPase, for which no FRET probe has been developed so far. Our model highlights for the first time the visualization of RhoB activation visualized in different cellular contexts: serum starvation and stimulation with growth factors that lead to the reorganization of the endosomal and membrane pool of RhoB. We show further that this cellular model is a robust and sensitive tool to study changes in RhoB activation profile in response to various stimulations, to the inhibition of GTPase regulators and upstream Rho GTPase signaling pathways. Together our results show that this strategy may be transposed to any protein-protein interaction and the screening of small-molecule and other factors that may modulate these interactions.

Results

Use of a Tripartite Split-GFP System to Monitor GTPase Activation.

Figure 1B:
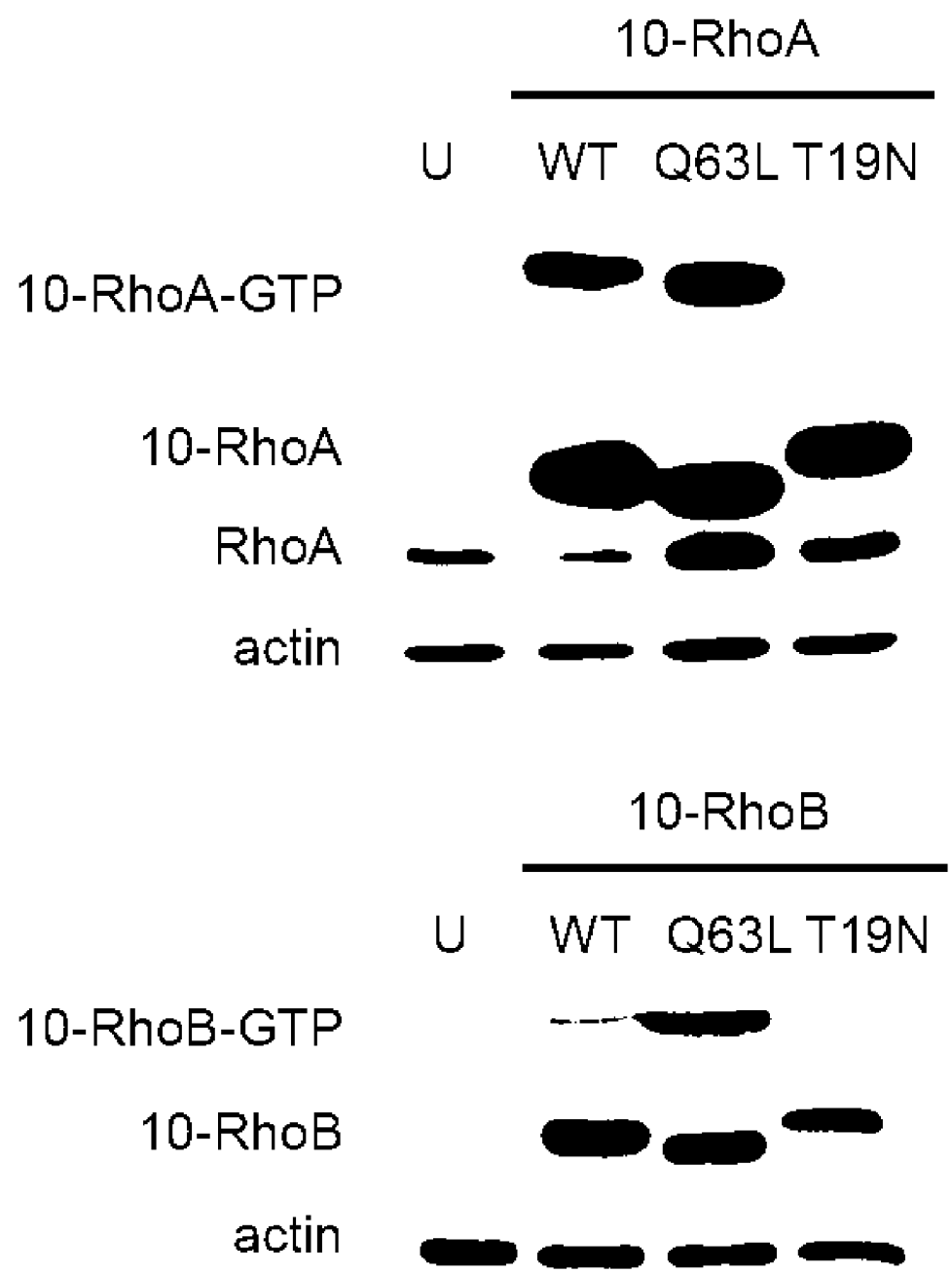
Figure 1C:
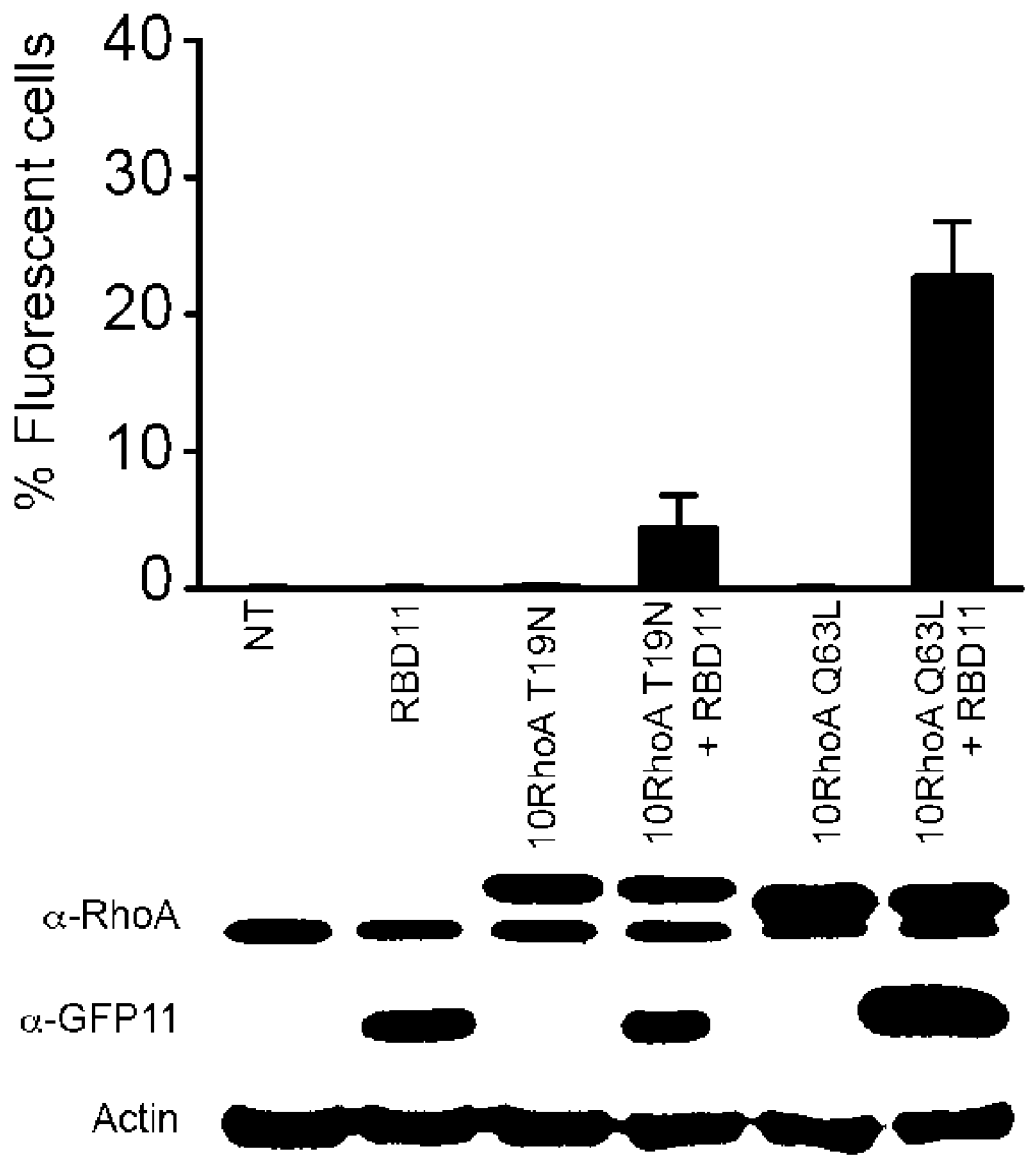
Figure 1C:
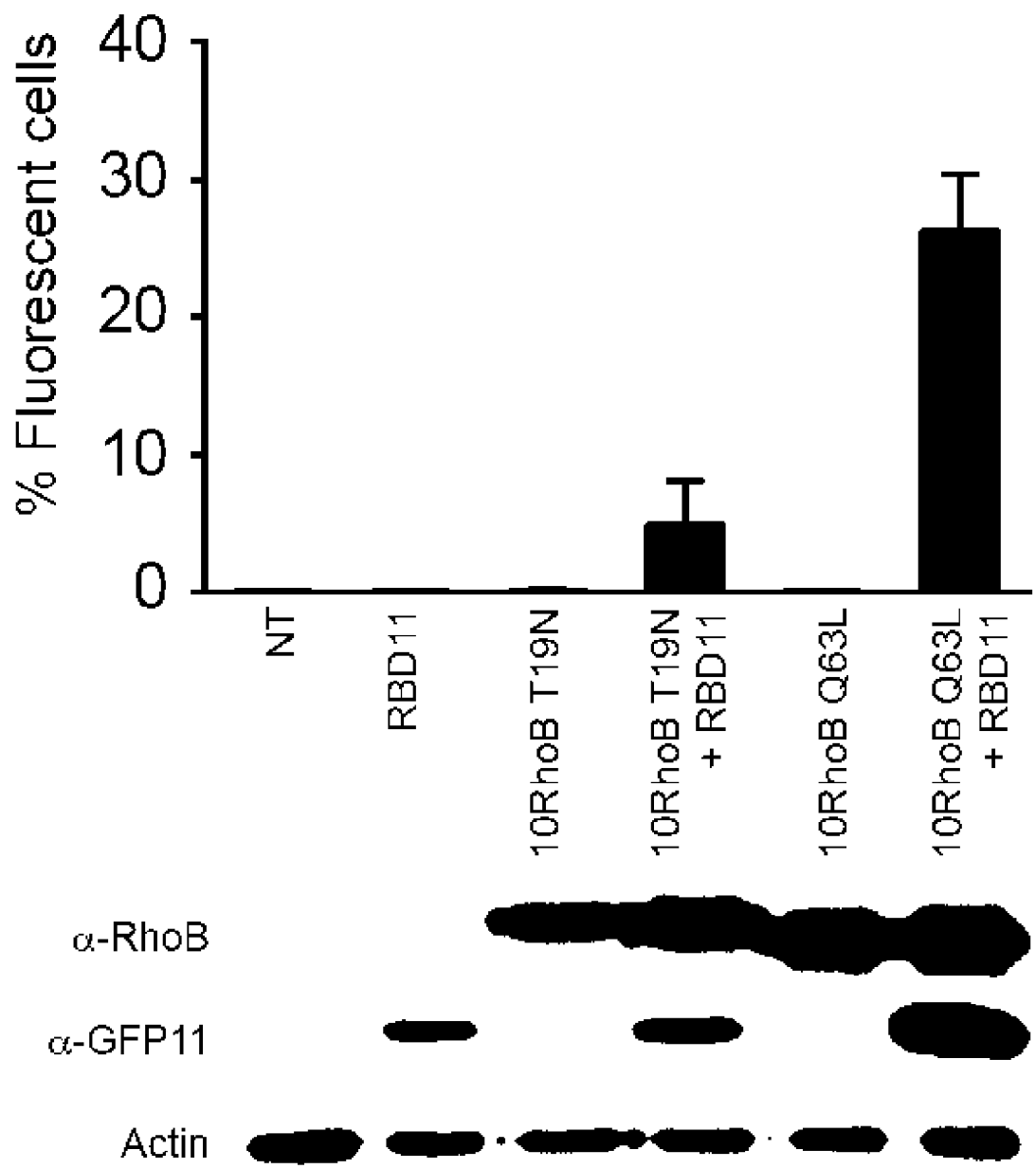
Figure 1C:
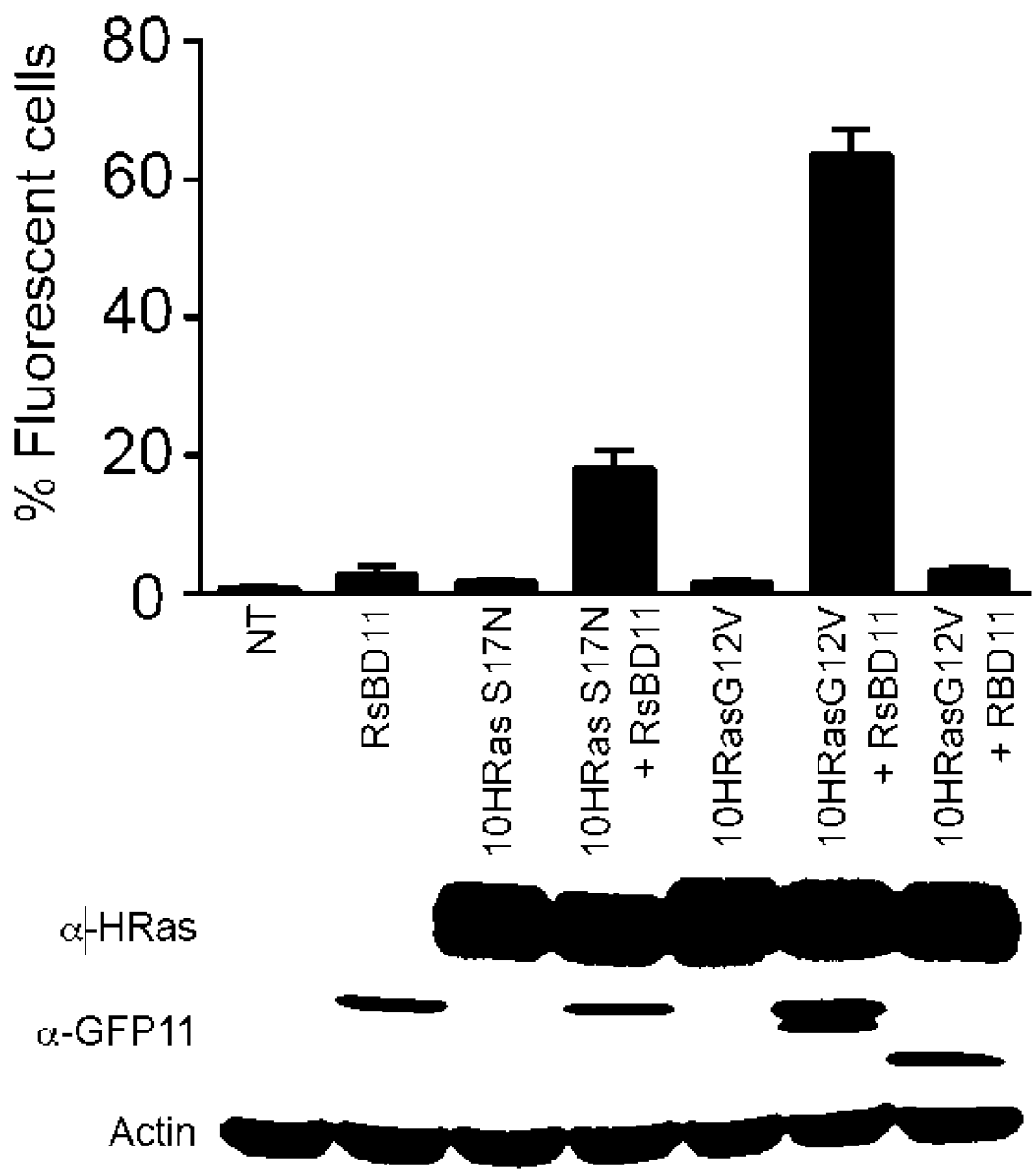
Figure 1D:
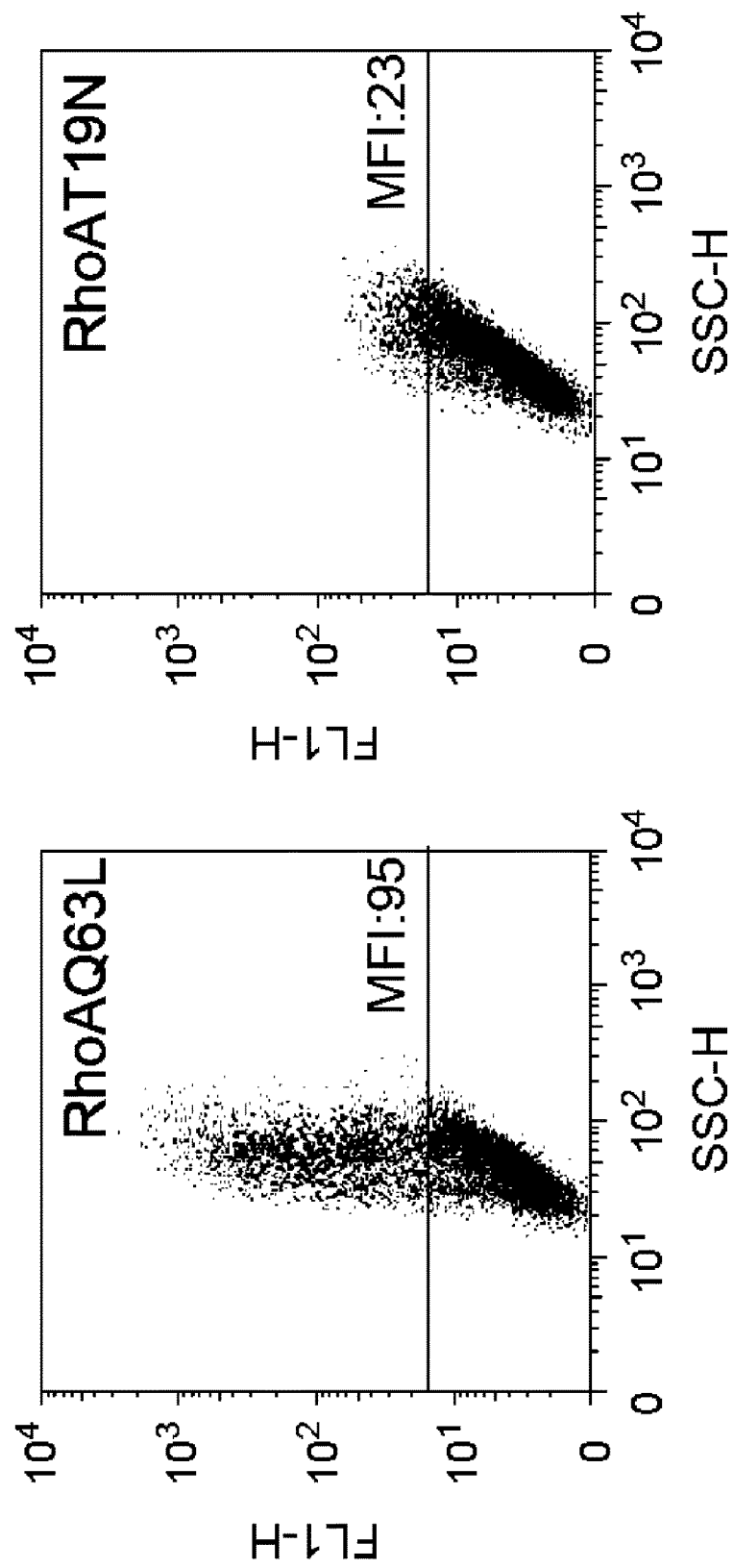
Figure 1D:
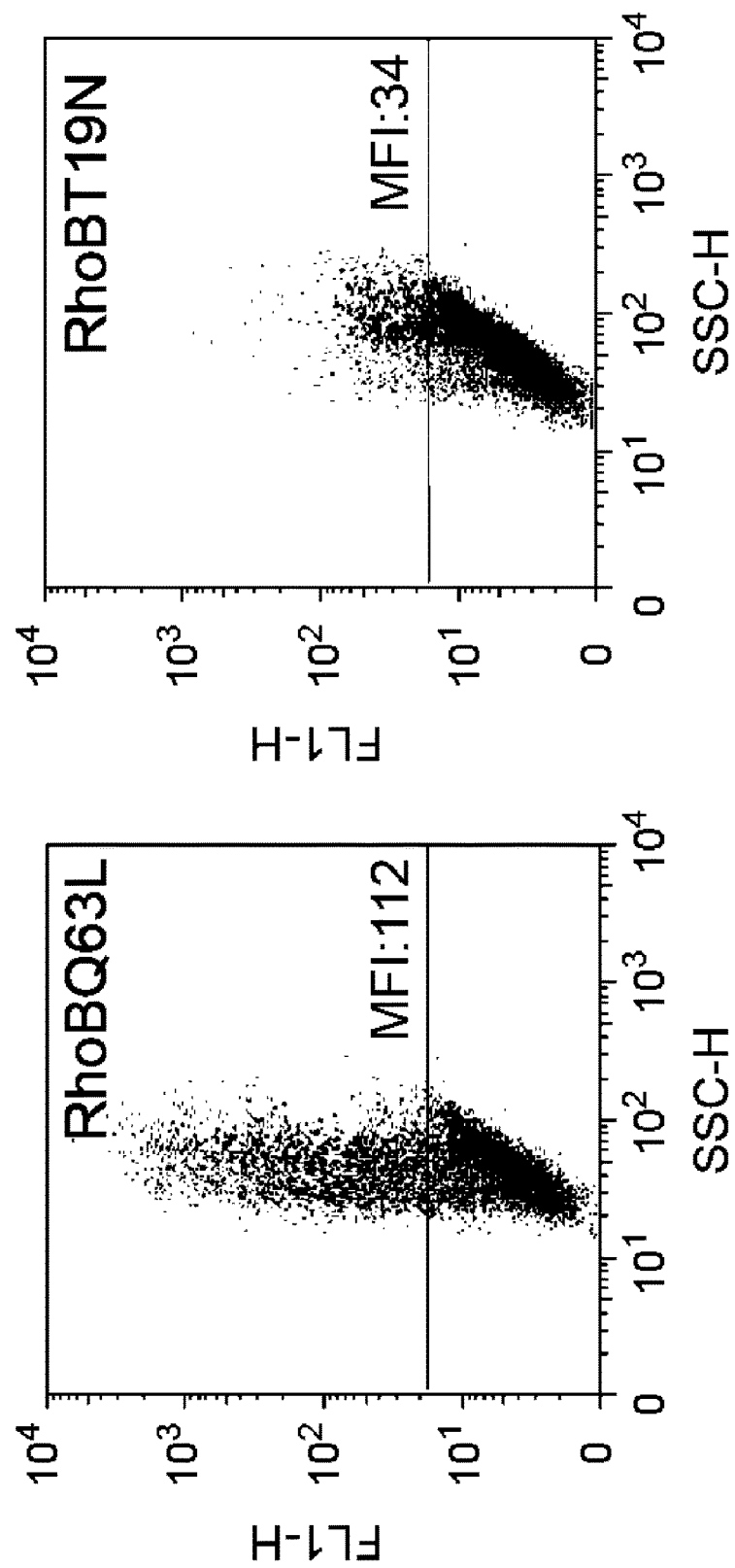
Figure 1D:
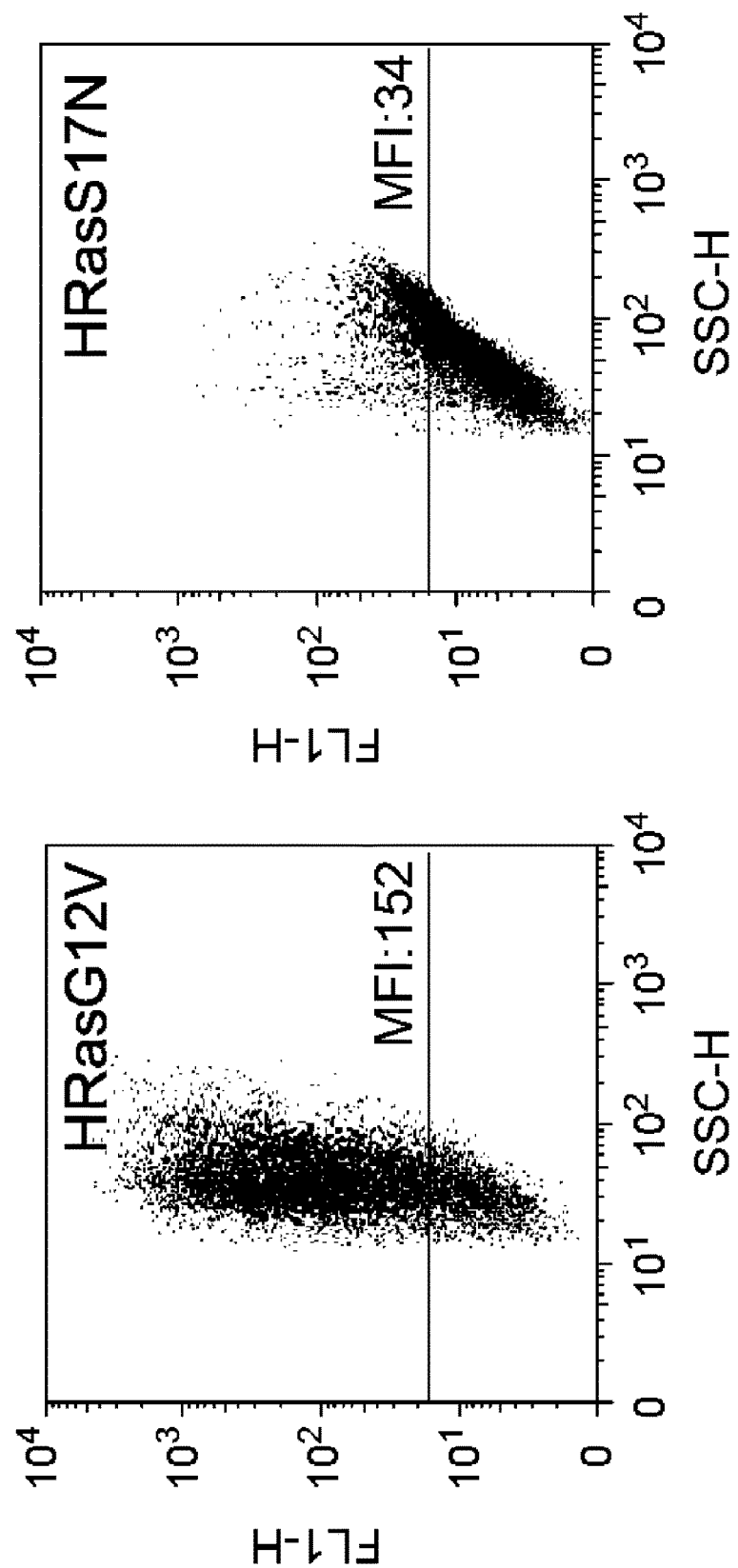

We first validated the tripartite split-GFP assay for studying GTPase activation by probing interactions of the GTPase and the GTPase-binding domain (GBD) of an effector protein. As binding to GBD is dependent on GTP-bound GTPase, this assay should give a fluorescence signal only when the GTPase is active (FIG. 1a). In a first step, we verified that the small GFP10 tag fused to two variants of Rho (RhoA and RhoB) did not interfere with its interaction with the Rho-binding domain (RBD) of the Rho specific effector Rhotekin in vitro using GST-Rhotekin-RBD pull-down assays. Accordingly, no binding was detected with the dominant negative variant of RhoA or RhoB (T19N), whereas pull-down assays using the wild-type protein or the constitutively active mutant (Q63L) indicated a substantial amount of bound GFP10-Rho (FIG. 1b). In parallel, we optimized a cell line that express homogenous and high levels of GFP1-9 fragment and produced polyclonal antibody sera to specifically detect the GFP10 and GFP11 tags. We then analyzed these interactions in living cells by co-expressing the GFP10-Rho fusions for the active mutant (Q63L) and the inactive variant of Rho (T19N) with the RBD-GFP11 effector domain. Flow cytometry analysis indicated a clear discrimination between the inactive and active mutants, showing a 5-fold induction for the GTP-bound Rho (FIGS. 1 c, c', c", d, d', d"). Only 5% of the cells expressing the dominant negative variant were fluorescent with intensities close to background level (FIGS. 1d, d', d"). To verify further the specificity of our assay, we performed similar activity measurements for H-Ras, a GTPase belonging to another subfamily. Similar induction ratio (≅3) was observed for interactions between GDP-bound (S17N) and GTP-bound (G12V) H-Ras mutants with the Ras-binding domain of the c-Raf effector protein (RsBD). This signal was highly specific as no fluorescence was detected upon co-expression of active H-Ras (G12V) with the unrelated Rho specific Rhotekin-binding domain (RBD) (FIG. 1c, c', c"). Analysis of the Rho-GTP/effector complexes by fluorescence microscopy indicated a correct localization for these variants, mostly at the plasma membrane of cells as previously described with fluorescent protein fusions[20,24]. In support of flow cytometry analysis, no fluorescent cells were detected upon co-expression of the Rho GDP-bound mutants and their effector binding domains, which are strictly described as non-binders.

Ideally, the assay should measure an induced activation of the wild-type protein. Because FRET biosensors have been extensively used to study the spatiotemporal activation of homologous RhoA[25], we verified that we could correctly report RhoA activity with the split-GFP system. We expressed the GFP10 tagged wild-type RhoA and RBD-GFP11 in HEK 293 cells expressing GFP1-9 (HEK 1-9) and induced starvation conditions (0% serum) for 24 H. We then measured at different time points the increase of the fluorescent cell population after stimulation with 10% bovine serum (FIG. 2). Flow cytometry analysis indicated a 1,5 fold increase in the percentage of fluorescent cells at 4 hours after stimulation, which accumulated over 8 h to double the number of fluorescent cells. Western blot analysis of corresponding cell extracts indicated no variation of total expressed RhoA protein in this time range (FIG. 2).

As Rho activity is strongly dependent on spatiotemporal signaling, we then investigated how the system would report the localization of active Rho. We co-expressed concomitantly the tripartite 10-RhoA and RBD-11 in HEK 1-9 cells in the presence of serum in order to localize RhoA active form. Our results indicated a global fluorescence signal at the plasma membrane, which correlates with the localization of active RhoA described in previous studies with Raichu probes[20]. Conversely, the detection of the global pool of expressed RhoA from a bipartite split-GFP assay (11-RhoA/1-10) uniformly showed a bright cytoplasmic fluorescence, correlating with the localization of a RhoA trapped by GDIα[25]. Together these results indicate the capability of the tripartite split-GFP assay to detect a variation in the global pool of activated Rho and to follow the activation of RhoGTPase in living cells.

Use of Anti-GFP VHH to Specifically Enhance Protein-Protein Interactions Signals Protein-protein interactions are preferably detected within living cells because they preserve the spatiotemporal information in the context of native physiology. Heterologous mammalian protein expression requires controlled expression systems that avoid toxicity and allow a better stability of the transgene. One drawback of genetically encoded fluorescence reporters is the limited sensitivity of the fluorescence in the context of low expression and in vivo imaging.

One single-domain antibody based on camelid heavy-chain antibodies (VHH G4) was discovered to improve the GFP fluorescence by modulating the spectral properties of wild-type GFP and enhanced eGFP[26]. Binding of the antibody to the GFP occurs with two residues of β-strands s7 and s8 (Asn146 and Arg168), adjacent to Ser205 and Glu222, which are conserved amino acids of β-strands s10 and s11, the two small tags used in our split-GFP reporter assay. As lowering expression of split-GFP fusions proteins resulted in fainter fluorescence signal, we wondered if such GFP intrabody would enhance the reconstituted GFP fluorescence. Using transient transfection, we co-expressed into HEK 293 cells the Myc-VHH anti-GFP nanobody with several variants of GFP1-9 targeted at specific subcellular compartments of the cell (membrane, nucleus, or cytoplasm) and analyzed the co-localization of both species. Interestingly, when GFP1-9 and the anti-GFP VHH were co-expressed, no co-localization was observed after immunostaining of both species. We then induced split-GFP complementation by introducing the non-prelocalized sandwich 10-RBD-11 (10-R-11) domain that associates spontaneously with GFP1-9. Concomitant to split-GFP complementation (ie green fluorescence) the anti-GFP VHH (anti-myc; red) co-localized uniformly with the reconstituted GFP1-9/GFP10_11. These data indicate that the anti-GFP antibody solely binds to the reconstituted split-GFP and not to GFP1-9 despite the presence of two nanobody interacting residues in the GFP1-9 scaffold[26].

We quantitatively measured if the co-expression of the anti-GFP nanobody would enhance split-GFP complementation. Several interacting and non-interacting pairs were chosen: specifically the 10-R-11 and 10-Zipper-11 (10-Z-11) chimeric domains as a titration of GFP1-9 expression, the known interacting 10-zipper/zipper-11, and the non-interacting 10-HRas/RBD-11 (see FIG. 1b). Flow cytometry analysis of transiently transfected plasmid fusions indicated a four fold increase in the mean fluorescence intensity of the positive cells that correlated with the split-GFP complementation fluorescence (FIG. 3). Indeed, the low fluorescence level of the non-interacting 10-HRas/RBD-11 was not modified in the presence of the antibody, indicating the VHH anti-GFP enhancer does not induce artificial split-GFP complementation. The G4 VHH domain may therefore be constitutively expressed in any GFP1-9 expressing cell lines without affecting background fluorescence.

A Cellular Model to Monitor Localization of Active RhoB

Unlike other Rho GTPases, no biosensor exists to study RhoB activation. Only constitutive active mutants (Q63L) fused to GFP have been used to exacerbate the dominant positive phenotype[27]. RhoB is a small GTPase whose expression is not constitutive but is generally induced by various stimuli such as growth factors, non-genotoxic and genotoxic stress[28-30]. Unlike its homologue RhoA, RhoB is poorly expressed in many cells lines and its overexpression results in a strong cell retraction and apoptosis. Moreover, expression of the effector domain has to be regulated in order to avoid excessive trapping of the Rho-GTP form. We therefore implemented an expression system in which both the GTPase and its effector-binding domain are expressed from two independent inducible promoters.

To achieve such model, we modified a tet-on inducible lentiviral backbone into an optimized a bidirectional tet-on vector pTRIP-TRE-BI. Immortalized human pulmonary fibroblasts (MRCS-SV) expressing constitutively both the GFP1-9 detector and the VHH anti-GFP domain were transduced with the Lv. pTRIP TRE-BI-10-Bwt/RBD-11 expression lentivirus to obtain the MRC5-RhoBact cell line. Expression levels of both GFP10-Rho and RBD-GFP11 fusions were modulated in order to minimize the toxicity and obtain a good signal/noise ratio of the RhoB activation biosensor fluorescence. The basal activation of RhoB was then evaluated in the MRC5-RhoBact expression cell line after a period of serum starvation of 24 to 48 H, and then re-stimulated by growth factors. Our results indicate a significant increase of 41.3% in the percentage of fluorescent cells after 4 H of stimulation with serum, indicating that the biosensor cellular model responds to the stimulation with growth factors. Fluorescence levels were similar in untreated cells at T0 and 4H, which indicates that there is no detectable change in RhoB activation due to the protein turnover in this time range. However, the strong percentage of fluorescence cells in basal conditions reflects a strong RhoB activation immediately after its expression. Indeed, studies on the endogenous protein have shown that RHOB is an immediate response gene to growth factors and other stress, with a rapid gain of its activity few minutes after its induction[30]. We next assessed the effect of inhibiting the basal RhoB activation by the exoenzyme C3 transferase, a Rho inhibitor that ADP ribosylates the Rho effector binding domain and blocks the binding to downstream effectors[31]. The addition of increasing concentrations of the cell-permeant recombinant TAT-C3 exoenzyme resulted in a progressive decrease of RhoB activation with a complete inhibition above 10 µg/ml of purified peptide. This result correlates with western blot analysis that shows RhoB protein mainly in ADP-ribosylated form at this concentration. Moreover, we could successfully monitor the inhibition of RhoB activation by measurement of the fluorescence in a 96-well microplate reader. All together our data validate further our model as a reporter of the direct RhoB/RBD protein-protein interaction, which can be successfully used for high-throughput screening of small molecule that modulates Rho activity.

RhoGTPase activation occurs with the binding of the GDP-bound Rho to GEF factors, which catalyze the release of GDP and its replacement with GTP nucleotide, converting the Rho GTPase into its active form[32]. We therefore evaluated if the Rho-split-GFP biosensor would be sensitive to the inhibition of upstream signaling and more specifically GEFs. To demonstrate our hypothesis, we chose to downregulate VAV2, a major Rho exchange factor that was shown to activate RhoB upon growth factor stimulation[33,34], downstream the EGF receptor[35]. siRNA downregulation of VAV2 in MRC5-RhoBact cells cultivated in serum-containing medium led to a marked decrease of 60% of the fluorescent cells measured by flow cytometry and observed by fluorescence microscopy. This result demonstrates that the Rho-splitGFP biosensor reports the decrease of Rho activation state upon the inhibition of an upstream activator, and validates the use of siRNA strategy on MRC5-RhoBact for screening Rho activator candidates. Interestingly, the reduction factor of fluorescent cells obtained upon VAV2 down-regulation (60% ie a reduction factor of 2.5) was above the induction factor observed after stimulation with serum (41.3% ie an increase factor of 1.6). These results suggest that the basal activation of RhoB due to overexpression of the protein is mediated through VAV2 exchange factor.

Localization of Active RhoB in Starved and Serum Stimulated Cells

Previous in vivo localization studies of RhoB fused to GFP reported RhoB at the plasma membrane and in endosomes[36-38]. These two localizations have been mainly attributed to the prenylation status of RhoB, with a geranylgeranylated (GG) form preferentially localized in the endosomes and a farnesylated (F) form at the plasma membrane[27,39,40]. We thought to investigate if these subcellular pools vary in function of RhoB activation. We used our cellular model to compare the localization of active RhoB in steady state conditions (0.1% BSA) where GTPases have a lowered activity, and in serum-enriched medium (10% FBS). Our biosensor was expressed for 48 h in both media with doxycycline and cells were imaged after fixation with 3,7% paraformaldehyde. Whereas active RhoB was present in endosomes and at the plasma membrane, the proportion of each species varied noticeably between both conditions. In serum free media, the fluorescence signal was significant in the cytoplasm, with 30% of the total fluorescence located in the vesicular pool. These proportions follow closely the vesicle distribution quantified previously by antibody staining of endogenous RhoB (Wherlock et al. 2004). By constrast, cells cultivated in serum-enriched medium indicated a decreased amount of active RhoB in vesicles (5% of total fluorescence) with a gain of fluorescence signal at the plasma membrane, more specifically at cell protrusions and fillipodia. F-actin labelling indicated a clear co-localization of RhoB-GTP along cortical actin cables with intensifications of the co-localization with cortical actin fibres in serum-cultivated cells. Similarly we observed a mostly complete localization of active RhoB with β-integrin, one of the major adhesion receptor of adherent cells used as plasma membrane marker[41]. In order to identify the vesicular compartments containing the active pool of RhoB, we performed co-staining experiments with several endocytic sub-compartments markers. In serum starvation conditions (BSA 0.1%), we observed partial co-localization with the early endosome-associated protein EEA1 and with the late endosomes marker Rab7, and to a lesser extend with the lysosomal protein LAMP1. Conversely, in serum stimulated cells, we noticed a loss of co-localization of active RhoB with early and late endosomes markers (EEA1 and Rab7 respectively) as well as with lysosomes marker LAMP1. These results are consistent with the decrease in vesicular active RhoB pool observed in serum-stimulated conditions.

To determine if the movements of RhoB-GTP positive endosomes are triggered by serum uptake to the plasma membrane, we performed time-lapse experiments in starved MRCS-RhoBact cells stimulated with 10% FBS. Focusing on faint fluorescent cells, we followed the increase of fluorescence after serum stimulation. Our results indicated a first phase that showed a ≅2-fold increase of split-GFP fluorescence that stalled progressively to reach a plateau. These results support our biosensor cell line as a robust cellular model to follow Rho activation after stimulation. Images of the same cell show an increase in fluorescence intensity at the plasma membrane that is accompanied with a rapid recycling activity of the endosome pool containing RhoB-GTP. Our results support Borja model[38], for which RhoB is rapidly activated following serum stimulation, which enables actin fiber elongation and the transport of RhoB-GTP to the cortical actin and the plasma membrane.

CONCLUSION

In this study, we described the improvement of the tripartite split-GFP assay for monitoring protein-protein interactions in cell-based assays. We exemplified the improvement of this method with the monitoring of small GTPase activation. In the following examples, we demonstrate the design of cellular models for different members of the Ras superfamily of small GTPases (Ras and Rho) to study the fine localization of their activation, the regulation of their activity by upstream signaling pathways and the effect of chemical and pharmacological compounds on their activity.

We have first shown that our system could efficiently discriminate between active and inactive GTPase state specifically by analyzing interactions with their cognate effector domain. We have also validated that although irreversible, these assay could monitor activation changes in the off-on state progression. In accordance with other methods for monitoring Rho activation such as FRET probes described for several Rho GTPases we could show that our sensor was correctly localized in the cell where GTPase activity is enhanced. In the examples described, the cellular model(s) developed to monitor GTPase activation combine the enhancer properties and controlled expression of RhoGTPase and their effector domains. Using that model, we could monitor an increase in the activation consequent to the stimulation of growth factor receptors, and identify the fine redistribution of active RhoB in various subcellular compartments of the cell. We also demonstrated that our approach let us decipher Rho signaling pathways by the downregulation of upstream activators of Rho and the study on subsequent Rho activation. Moreover, we demonstrate the direct inhibition of Rho effector interactions by a large spectrum Rho inhibitor, which is in favor of the robustness of the model for large scale screening of agents (small molecules, peptides) that would disfavor or interrupt protein-protein interactions.

We have developed a new strategy to improve the sensitivity of the tripartite split-GFP assay, by integrating in the reporter cell line a VHH antibody that enhance the fluorescence of the complemented GFP[26]. Co-expression of the VHH domain induced an improvement in the reconstituted GFP fluorescence by a factor 4, whereas there is no significant increase with full length eGFP, as previously described $(1,1)^{26}$. Mechanisms of enhancing properties of the nanobody on the reconstituted split-GFP may not simply be due to a single effect on the spectral properties of the chromophore as split-GFP variants have been engineered from Superfolder GFP that already possess the S65T mutation (the red shifted eGFP mutation). As the nanobody does not recognize the GFP1-9 fragment alone, it is likely that the GFP1-9 expressed alone adopt a totally distinct conformation from the GFP barrel-like structure. It is only when the complementation occurs, that the GFP barrel is reformed and the chromophore is matured. Binding of the VHH intrabody might improve this maturation by stabilizing the chromophore environment that is dependent on contacts with residues located within GFP10 and GFP11 β-strands, and by strengthening the interactions between residues essential for efficient chromophore formation.

Consequently, our approach for improving tripartite split-GFP assay led us to define a model that comprises a protein complex of two proteins respectively tagged with the GFP10 and GFP11 peptides that associate with the detection fragment GFP1-9. Upon binding with GFP10 and GFP11, the GFP1-9 conformation changes and binds to the VHH anti GFP antibody, which improves chromophore formation and maturation. The protein complex may be composed of any interacting proteins. This interaction may be either constitutive or induced by phosphorylation, acetylation, etc. . . . which modifies the proteins interaction profile.

REFERENCES

Throughout this application, various references describe the state of the art to which this invention pertains. The disclosures of these references are hereby incorporated by reference into the present disclosure.

1. Day, R. N. & Davidson, M. W. The fluorescent protein palette: tools for cellular imaging. *Chem Soc Rev* 38, 2887-2921 (2009).
2. Pfleger, K. D. & Eidne, K. A. Illuminating insights into protein-protein interactions using bioluminescence resonance energy transfer (BRET). *Nat Methods* 3, 165-174 (2006).

3. Pelletier, J. N., Arndt, K. M., Pluckthun, A. & Michnick, S. W. An in vivo library-versus-library selection of optimized protein-protein interactions. *Nat Biotechnol* 17, 683-690 (1999).
4. Rossi, F., Charlton, C. A. & Blau, H. M. Monitoring protein-protein interactions in intact eukaryotic cells by beta-galactosidase complementation. *Proc Natl Acad Sci U.S.A.* 94, 8405-8410 (1997).
5. Galarneau, A., Primeau, M., Trudeau, L. E. & Michnick, S. W. Beta-lactamase protein fragment complementation assays as in vivo and in vitro sensors of protein protein interactions. *Nat Biotechnol* 20, 619-622 (2002).
6. Shekhawat, S. S. & Ghosh, I. Split-protein systems: beyond binary protein-protein interactions. *Curr Opin Chem Biol* 15, 789-797 (2011).
7. Hu, C. D. & Kerppola, T. K. Simultaneous visualization of multiple protein interactions in living cells using multicolor fluorescence complementation analysis. *Nat Biotechnol* 21, 539-545 (2003).
8. Paulmurugan, R. & Gambhir, S. S. Firefly luciferase enzyme fragment complementation for imaging in cells and living animals. *Anal Chem* 77, 1295-1302 (2005).
9. Paulmurugan, R. & Gambhir, S. S. Novel fusion protein approach for efficient high-throughput screening of small molecule-mediating protein-protein interactions in cells and living animals. *Cancer Res* 65, 7413-7420 (2005).
10. Cassonnet, P., et al. Benchmarking a luciferase complementation assay for detecting protein complexes. *Nat Methods* 8, 990-992 (2011).
11. Zilian, E. & Maiss, E. An optimized mRFP-based bimolecular fluorescence complementation system for the detection of protein-protein interactions in planta. *J Virol Methods* 174, 158-165 (2011).
12. Cabantous, S., Terwilliger, T. C. & Waldo, G. S. Protein tagging and detection with engineered self-assembling fragments of green fluorescent protein. *Nat Biotechnol* 23, 102-107 (2005).
13. Remy, I. & Michnick, S. W. A highly sensitive protein-protein interaction assay based on Gaussia luciferase. *Nat Methods* 3, 977-979 (2006).
14. Morell, M., Espargaro, A., Aviles, F. X. & Ventura, S. Detection of transient protein-protein interactions by bimolecular fluorescence complementation: the Abl-SH3 case. *Proteomics* 7, 1023-1036 (2007).
15. Cabantous, S., Nguyen H, Pedelacq J D, Koraïchi F., Chaudary A, Ganguly K G., Favre G., Terwilliger, T. C. & Waldo, G. S*. A new protein-protein interaction sensor based on tripartite split-GFP association. *Sci. Rep. In revision* (2013).
16. Valencia, A., Chardin, P., Wittinghofer, A. & Sander, C. The ras protein family: evolutionary tree and role of conserved amino acids. *Biochemistry* 30, 4637-4648 (1991).
17. Ellenbroek, S. I. & Collard, J. G. Rho GTPases: functions and association with cancer. *Clin Exp Metastasis* 24, 657-672 (2007).
18. Vega, F. M. & Ridley, A. J. Rho GTPases in cancer cell biology. *FEBS Lett* 582, 2093-2101 (2008).
19. Pertz, O. & Hahn, K. M. Designing biosensors for Rho family proteins-deciphering the dynamics of Rho family GTPase activation in living cells. *J Cell Sci* 117, 1313-1318 (2004).
20. Machacek, M., et al. Coordination of Rho GTPase activities during cell protrusion. *Nature* 461, 99-103 (2009).
21. Nakamura, T., Kurokawa, K., Kiyokawa, E. & Matsuda, M. Analysis of the spatiotemporal activation of rho GTPases using Raichu probes. *Methods Enzymol* 406, 315-332 (2006).
22. Lu, A., et al. A clathrin-dependent pathway leads to KRas signaling on late endosomes en route to lysosomes. *J Cell Biol* 184, 863-879 (2009).
23. Cabantous, S., et al. A New Protein-Protein Interaction Sensor Based on Tripartite Split-GFP Association. *Sci Rep* 3, 2854 (2013).
24. Mochizuki, N., et al. Spatio-temporal images of growth-factor-induced activation of Ras and Rap1. *Nature* 411, 1065-1068 (2001).
25. Pertz, O., Hodgson, L., Klemke, R. L. & Hahn, K. M. Spatiotemporal dynamics of RhoA activity in migrating cells. *Nature* 440, 1069-1072 (2006).
26. Kirchhofer, A., et al. Modulation of protein properties in living cells using nanobodies. *Nat Struct Mol Biol* 17, 133-138 (2010).
27. Wherlock, M., Gampel, A., Futter, C. & Mellor, H. Farnesyltransferase inhibitors disrupt EGF receptor traffic through modulation of the RhoB GTPase. *J Cell Sci* 117, 3221-3231 (2004).
28. Fritz, G. & Kaina, B. Transcriptional activation of the small GTPase gene rhoB by genotoxic stress is regulated via a CCAAT element. *Nucleic Acids Res* 29, 792-798 (2001).
29. Mircescu, H., et al. Identification and characterization of a novel activated RhoB binding protein containing a PDZ domain whose expression is specifically modulated in thyroid cells by cAMP. *Eur J Biochem* 269, 6241-6249 (2002).
30. Canguilhem, B., et al. RhoB protects human keratinocytes from UVB-induced apoptosis through epidermal growth factor receptor signaling. *J Biol Chem* 280, 43257-43263 (2005).
31. Wilde, C., Genth, H., Aktories, K. & Just, I. Recognition of RhoA by Clostridium botulinum C3 exoenzyme. *J Biol Chem* 275, 16478-16483 (2000).
32. Rossman, K. L., Der, C. J. & Sondek, J. GEF means go: turning on RHO GTPases with guanine nucleotide-exchange factors. *Nat Rev Mol Cell Biol* 6, 167-180 (2005).
33. Thalappilly, S., Soubeyran, P., Iovanna, J. L. & Dusetti, N. J. VAV2 regulates epidermal growth factor receptor endocytosis and degradation. *Oncogene* 29, 2528-2539 (2010).
34. Liu, B. P. & Burridge, K. Vav2 activates Rac1, Cdc42, and RhoA downstream from growth factor receptors but not beta1 integrins. *Mol Cell Biol* 20, 7160-7169 (2000).
35. Gampel, A. & Mellor, H. Small interfering RNAs as a tool to assign Rho GTPase exchange-factor function in vivo. *Biochem J* 366, 393-398 (2002).
36. Mellor, H., Flynn, P., Nobes, C. D., Hall, A. & Parker, P. J. PRK1 is targeted to endosomes by the small GTPase, RhoB. *J Biol Chem* 273, 4811-4814 (1998).
37. Michaelson, D., et al. Differential localization of Rho GTPases in live cells: regulation by hypervariable regions and RhoGDI binding. *J Cell Biol* 152, 111-126 (2001).
38. Fernandez-Borja, M., Janssen, L., Verwoerd, D., Hordijk, P. & Neefjes, J. RhoB regulates endosome transport by promoting actin assembly on endosomal membranes through Dial. *J Cell Sci* 118, 2661-2670 (2005).
39. Lebowitz, P. F. & Prendergast, G. C. Functional interaction between RhoB and the transcription factor DB1. *Cell Adhes Commun* 6, 277-287 (1998).
40. Milia, J., et al. Farnesylated RhoB inhibits radiation-induced mitotic cell death and controls radiation-induced centrosome overduplication. *Cell Death Differ* 12, 492-501 (2005).
41. Del Pozo, M. A., et al. Integrins regulate GTP-Rac localized effector interactions through dissociation of Rho-GDI. *Nat Cell Biol* 4, 232-239 (2002).

The invention claimed is:

1. A method for detecting the binding between a polypeptide (A) and a polypeptide (B) in a cell comprising:

i) providing a cell that expresses:

(a) a GFP1-9 polypeptide comprising an amino acid sequence having at least 90% of identity with the amino acid sequence selected from the group consisting of SEQ ID NO:1-4

(b) a first fusion protein comprising polypeptide (A) fused to a GFP10 polypeptide having an amino acid sequence having at least 90% identity with an amino acid sequence selected from the group consisting of SEQ ID NO:5-7

(c) a second fusion protein comprising polypeptide (B) fused to a GFP11 polypeptide having an amino acid sequence having at least 90% identity with an amino acid sequence selected from the group consisting of SEQ ID NO:8-9 and (d) an intrabody specific for the complex formed by the self-assembly of the first polypeptide, (a), the first fusion protein (b) and the second fusion protein (c), wherein the intrabody is a single domain antibody comprising the three complementarity determining regions (CDRs) of SEQ ID NO: 16; and ii) detecting fluorescence, wherein when the fluorescence is detected it is concluded that polypeptide (A) binds to polypeptide (B) and when the fluorescence is not detected it is concluded that the polypeptide (A) does not bind to polypeptide (B)

wherein the polypeptide (A) is a GTPase and the polypeptide B is a GTPase binding domain (GBD) or vice versa.

2. The method of claim 1 wherein the GFP1-9 polypeptide consists of the amino acid sequence set forth in SEQ ID NO:1, 2, 3, or 4.

3. The method of claim 1 wherein the GFP1-9 polypeptide is fused to a subcellular targeting sequence of interest, such that the fragment is localized to the subcellular element of interest, following expression of the fragment in the cell or transfection into the cell.

4. The method of claim 1 wherein the polypeptide (A) or (B) is fused either directly or via a spacer at its C-terminal end to the N-terminal end of the heterologous detector polypeptide, or at its N-terminal end to the C-terminal end of the heterologous detector polypeptide.

5. The method of claim 1 wherein the GFP10 polypeptide consists of the amino acid sequence set forth in SEQ ID NO:5, 6, or 7.

6. The method of claim 1 wherein the GFP11 polypeptide consists of the amino acid sequence set forth in SEQ ID NO:8 or 9.

7. The method of claim 1 wherein the first fusion protein consists of the amino acid sequence set forth in SEQ ID NO:10, 11, 12, 13, 17 or 18.

8. The method of claim 1 wherein the second fusion protein consists of the amino acid sequence set forth in SEQ ID NO: 14, 15 or 19.

9. The method of claim 1 wherein the intrabody is a single domain antibody.

10. The method of claim 1 wherein the intrabody is a single domain antibody comprising an amino acid sequence having at least 90% of identity with the amino acid sequence set forth in SEQ ID NO:16.

11. The method of claim 1 wherein the intrabody is fused to a heterologous polypeptide to form fusion protein.

12. The method of claim 11 wherein the heterologous polypeptide is a fluorescent polypeptide.

13. The method of claim 1 wherein the intrabody is conjugated with a detectable label.

14. The method of claim 1 wherein the polypeptide (A) is a GTPase and the polypeptide B is a GTPase binding domain (GBD).

15. The method of claim 1 which further comprises determining the subcellular localization of the emitted fluorescence.

16. The method of claim 12, wherein the fluorescent polypeptide is a green or red fluorescent protein (GFP or RFP).

* * * * *